(12) United States Patent
Anzai et al.

(10) Patent No.: US 12,016,979 B2
(45) Date of Patent: Jun. 25, 2024

(54) METHOD FOR PRODUCING ARTIFICIAL LUNG AND ARTIFICIAL LUNG

(71) Applicant: TERUMO KABUSHIKI KAISHA, Tokyo (JP)

(72) Inventors: Takao Anzai, Kanagawa (JP); Takayuki Kido, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 1323 days.

(21) Appl. No.: 16/567,072

(22) Filed: Sep. 11, 2019

(65) Prior Publication Data

US 2020/0000978 A1 Jan. 2, 2020

Related U.S. Application Data

(63) Continuation of application No. PCT/JP2018/000295, filed on Jan. 10, 2018.

(30) Foreign Application Priority Data

Mar. 14, 2017 (JP) .................................. 2017-048240

(51) Int. Cl.
*A61L 33/06* (2006.01)
*B01D 63/02* (2006.01)
*B01D 67/00* (2006.01)

(52) U.S. Cl.
CPC .............. *A61L 33/06* (2013.01); *B01D 63/02* (2013.01); *A61L 2300/42* (2013.01); *A61L 2420/02* (2013.01); *B01D 67/00* (2013.01)

(58) Field of Classification Search
CPC ..... B29C 66/41; B29C 66/40; B29C 65/7838; B29C 65/78; B29C 59/021; B29C 51/006;
(Continued)

(56) References Cited

U.S. PATENT DOCUMENTS 6,495,101 B1 12/2002 Yokoyama et al.

FOREIGN PATENT DOCUMENTS

| EP | 0908191 A1 | 4/1999 |
| JP | H01180205 A | 7/1989 |

(Continued)

OTHER PUBLICATIONS

International Search Report (with English translation) and Written Opinion issued in corresponding International Patent Application No. PCT/JP2018/000295, 7 pages (Feb. 13, 2018).
(Continued)

*Primary Examiner* — Stella K Yi
(74) *Attorney, Agent, or Firm* — BUCHANAN INGERSOLL & ROONEY PC

(57) ABSTRACT

A method is disclosed for producing an artificial lung including a plurality of porous hollow fiber membranes for gas exchange which have an outer surface, an inner surface forming a lumen, and an opening portion communicating the outer surface with the inner surface. The method includes bringing any of the outer surface and the inner surface into contact with a colloidal solution that contains an antithrombotic high-molecular compound to circulate carbon dioxide gas to a side of the other surface. According to the present disclosure, an artificial lung can be produced in which a coating amount of antithrombotic high-polymer material (an antithrombotic high-molecular compound) on a hollow fiber membrane is increased.

16 Claims, 8 Drawing Sheets

(58) Field of Classification Search
CPC ... B29C 51/00; B29C 49/0031; B29C 48/901; B29C 48/151; B29C 2045/1726; B29C 45/1704; B29C 2045/14524; B29C 70/10
See application file for complete search history.

(56) References Cited

FOREIGN PATENT DOCUMENTS

| | | | |
|---|---|---|---|
| JP | H03261481 A | | 11/1991 |
| JP | H11114056 A | | 4/1999 |
| JP | 2006288866 A | | 10/2006 |
| JP | 4317183 | * | 8/2009 |
| WO | 2016143752 A1 | | 9/2016 |

OTHER PUBLICATIONS

An English Translation of the International Search Report (Form PCT/ISA/210) and the Written Opinion of the International Searching Authority (Form PCT/ISA/237) dated Feb. 13, 2018, by the Japanese Patent Office in corresponding International Application No. PCT/JP2018/000295. (5 pages).

* cited by examiner

FIG. 8

Table 1

|  | Coating solution (concentration) | Carbon dioxide gas circulating condition | | Coating amount of PMEA on artificial lung membrane (mg/m²) |
|---|---|---|---|---|
|  |  | Flow rate (L/min) | Circulating time (min) |  |
| Example 2-1 | Artificial Lung (1) | Coating solution (1) (0.1% by mass) | 2 | 2 | 20.2 |
| Example 2-2 | Artificial Lung (2) | Coating solution (1) (0.1% by mass) | 2 | 10 | 35.9 |
| Example 2-3 | Artificial Lung (3) | Coating solution (1) (0.1% by mass) | 2 | 60 | 50.3 |
| Comparative Example 2-1 | Artificial Lung (4) | Coating solution (1) (0.1% by mass) | No circulation, left to stand for 2 minutes | | 5.7 |
| Comparative Example 2-2 | Artificial Lung (5) | Coating solution (2) (0.3% by mass) | No circulation, left to stand for 2 minutes | | 8.3 |

FIG. 9

Table 2

|  |  | Coating solution (concentration) | Carbon dioxide gas circulating condition | | Coating amount of PMEA on artificial lung membrane (mg/m²) | Maintenance rate of the number of platelets after circulation for 30 minutes (%) |
|---|---|---|---|---|---|---|
|  |  |  | Flow rate (L/min) | Circulating time (min) |  |  |
| Example 2-1 | Artificial Lung (1) | Coating solution (1) (0.1% by mass) | 2 | 2 | 20.2 | 97 |
| Comparative Example 2-1 | Artificial Lung (4) | Coating solution (1) (0.1% by mass) | No circulation, left to stand for 2 minutes | | 5.7 | 63 |

METHOD FOR PRODUCING ARTIFICIAL LUNG AND ARTIFICIAL LUNG

CROSS-REFERENCES TO RELATED APPLICATIONS

This application is a continuation of International Application No. PCT/JP2018/000295 filed on Jan. 10, 2018, which claims priority to Japanese Application No. 2017-048240 filed on Mar. 14, 2017, the entire content of both of which is incorporated herein by reference.

TECHNICAL FIELD

The present disclosure relates to a method for producing an artificial lung and an artificial lung. In more detail, the present disclosure relates to a method for producing a hollow fiber membrane type artificial lung for removing carbon dioxide in the blood and adding oxygen to the blood in extracorporeal blood circulation, for example, a hollow fiber membrane artificial lung of an outside blood flow type; and relates an artificial lung.

BACKGROUND DISCUSSION

A hollow fiber membrane type artificial lung using porous membranes generally can be used as an extracorporeal circulator or an artificial heart-lung apparatus for assisting circulation in open heart surgery for a heart disease. The hollow fiber membranes can be used for membrane type artificial lungs. Gas exchange in blood is performed through these hollow fiber membranes. As a system of blood flow to the artificial lung, there are an inside flow system in which the blood flows inside of the hollow fiber membranes and gas flows outside of the hollow fiber membranes, and an outside flow system in which, by comparison, the blood flows outside of the hollow fiber membranes and gas flows inside of the hollow fiber membranes.

In hollow fiber membrane type artificial lungs, inner surfaces or outer surfaces of the hollow fiber membranes are in contact with the blood. Therefore, there is a concern that the inner surfaces or the outer surfaces of the hollow fiber membranes in contact with the blood may affect adhesion (attachment) or activation of the platelet system. For example, an outside flow type artificial lung in which the outer surfaces of the hollow fiber membranes are in contact with the blood can generate a blood flow, which can cause adhesion (attachment) or activation of the platelet system.

Considering such problems, and in view of the suppression and prevention effects of alkoxyalkyl (meth)acrylate on adhesion or activation of the platelet system, alkoxyalkyl (meth)acrylate can be used as an antithrombotic material for coating the hollow fiber membranes of an outside flow type artificial lung. For example, JP-A-1999-114056 (corresponding to Specification of U.S. Pat. No. 6,495,101 and Specification of European Patent No. 0908191) discloses that an outer surface or an outer surface layer of a hollow fiber membrane is coated with a coating solution obtained by dissolving a polymer containing alkoxyalkyl (meth)acrylate as a main component in a mixed solvent of water, methanol, and ethanol, and then dried.

International Publication No. WO2016/143752 discloses a technique for coating a hollow fiber membrane with a colloidal solution of a high-polymer material having antithrombotic properties as a technique capable of suppressing leakage of plasma components (plasma leakage) after blood circulation. According to this technique, an artificial lung can be obtained that can effectively suppress the leakage of plasma components by adjusting an average particle diameter of colloids to a specific ratio or more with respect to a diameter of an opening portion of a hollow fiber membrane, regardless of systems of blood flow.

Meanwhile, for the purpose of further reducing burdens on a patient, there is a demand for an artificial lung in which a coating amount of antithrombotic high-polymer material (an antithrombotic high-molecular compound) on a hollow fiber membrane is increased in order to improve antithrombotic properties.

SUMMARY

A method is disclosed for producing an artificial lung in which a coating amount of antithrombotic high-polymer material (an antithrombotic high-molecular compound) on a hollow fiber membrane can be increased.

In accordance with an exemplary embodiment, it was found that, when one surface of a hollow fiber membrane is brought into contact with a colloidal solution of an antithrombotic high-molecular compound, circulating carbon dioxide gas to a side of the other surface of the hollow fiber membrane can solve the above problems.

In accordance with an exemplary aspect, a method is disclosed for producing an artificial lung including a plurality of porous hollow fiber membranes for gas exchange which have an outer surface, an inner surface forming a lumen, and an opening portion communicating the outer surface with the inner surface, the method including a step of bringing any of the outer surface and the inner surface into contact with a colloidal solution that contains an antithrombotic high-molecular compound to circulate carbon dioxide gas to a side of the other surface.

In accordance with another aspect, a method is disclosed for producing an artificial lung including a plurality of porous hollow fiber membranes for gas exchange, the plurality of porous hollow fiber membranes having an outer surface, an inner surface forming a lumen, and an opening portion communicating the outer surface with the inner surface, the method comprising: bringing the outer surface or the inner surface into contact with a colloidal solution that contains an antithrombotic high-molecular compound; and circulating carbon dioxide gas on a side opposite of the outer surface or the inner surface that is being brought into contact with the colloidal solution containing the antithrombotic high-molecular compound.

In accordance with a further aspect, a method is disclosed for producing an artificial lung including a plurality of porous hollow fiber membranes for gas exchange, the plurality of porous hollow fiber membranes having an outer surface, an inner surface forming a lumen, and an opening portion communicating the outer surface with the inner surface, the method comprising: coating the outer surface of the plurality of porous hollow fiber membranes with a colloidal solution that contains an antithrombotic high-molecular compound; and circulating a carbon dioxide gas on the inner surface of the plurality of porous hollow fiber membranes.

In accordance with a further aspect, an artificial lung is disclosed comprising: a plurality of porous hollow fiber membranes for gas exchange, the plurality of porous hollow fiber membranes having an outer surface, an inner surface forming a lumen, and an opening portion communicating the outer surface with the inner surface; and wherein one of the outer surface and the inner surface has a coating in which an antithrombotic high-molecular compound is contained in an amount of 10 mg/m² surface or more.

BRIEF DESCRIPTION OF DRAWINGS

FIG. 8 is Table 1 showing test results from a plurality of examples and comparative examples with different carbon dioxide gas circulating condition and coating amount of polymethoxyethyl acrylate (PMEA) on artificial lung membranes.

FIG. 9 is Table 2 showing results illustrating that the antithrombotic properties of artificial lungs produced by a method according to the present disclosure show significant improvement by increasing the coating amount of PMEA.

DESCRIPTION OF EMBODIMENTS

Figure 1:
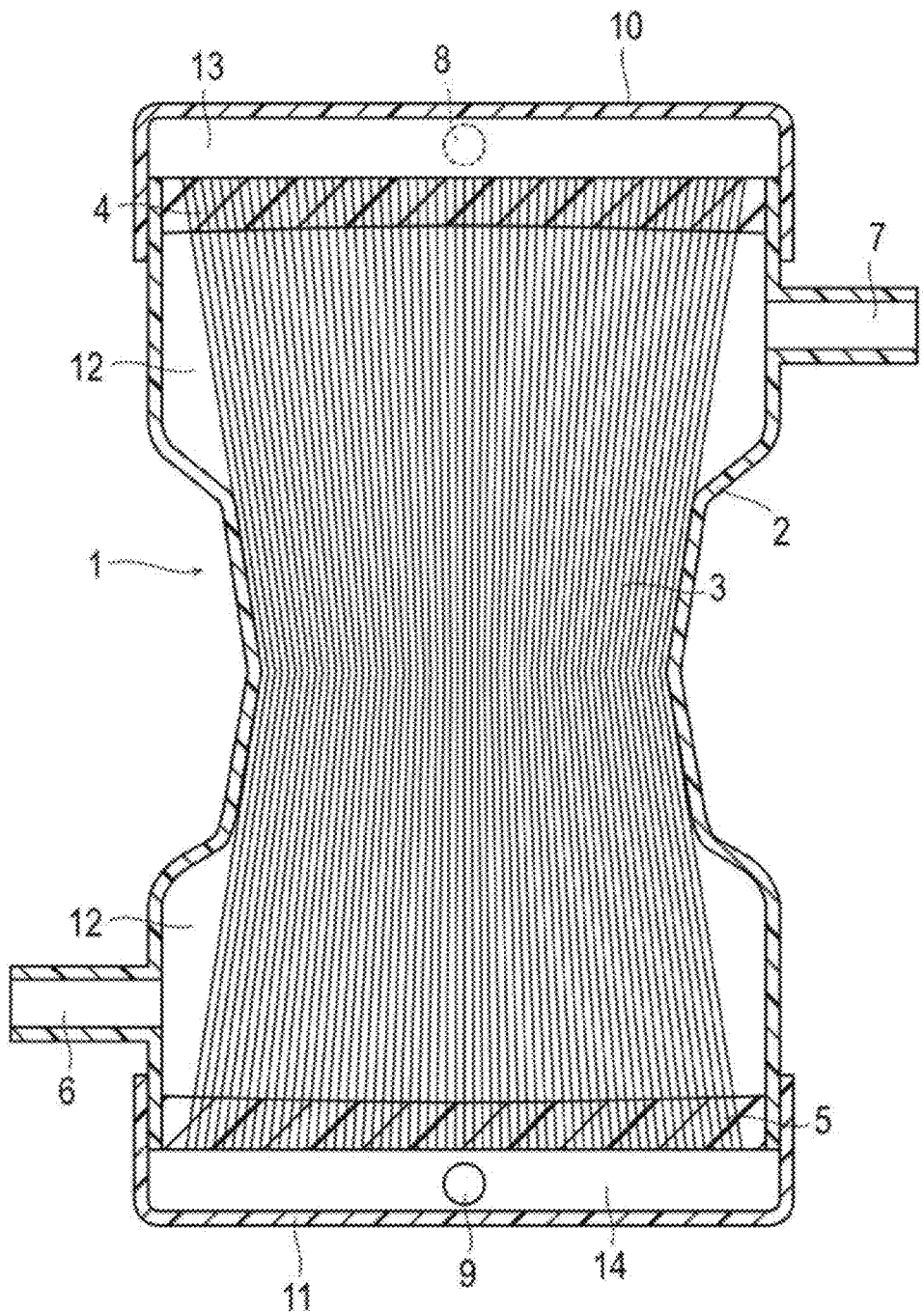
FIG. 1 is a cross-sectional view showing one embodiment of a hollow fiber membrane artificial lung of an outside blood flow type according to the present disclosure.

The present disclosure relates to a method for producing an artificial lung including a plurality of porous hollow fiber membranes for gas exchange which have an outer surface, an inner surface forming a lumen, and an opening portion communicating the outer surface with the inner surface, the method including a step of bringing any of the outer surface and the inner surface into contact with a colloidal solution that contains an antithrombotic high-molecular compound to circulate carbon dioxide gas to a side of the other surface. According to the present disclosure, it is possible to produce an artificial lung in which a coating amount of antithrombotic high-polymer material (an antithrombotic high-molecular compound) on a hollow fiber membrane is increased.

In the method for producing an artificial lung according to the present disclosure, by bringing any of the outer surface and the inner surface of porous hollow fiber membranes for gas exchange into contact with a colloidal solution that contains an antithrombotic high-molecular compound to circulate carbon dioxide gas to a side of the other surface (i.e., opposite surface), a coating amount of the antithrombotic high-molecular compound can be increased.

According to the technique of International Publication No. WO2016/143752, a hollow fiber membrane is coated with a colloidal solution of an antithrombotic high-molecular compound. It is perceived that, in this case, colloidal particles (particle surfaces) of the antithrombotic high-molecular compound contained in the colloidal solution are negatively charged, and cations are present around the colloidal particle to neutralize this charge. In other words, it is presumed that the colloidal particles are in a state of forming an electric double layer. In addition, the cations play a role of adsorbing colloidal particles to a surface of a negatively charged hollow fiber membrane.

In accordance with an exemplary embodiment, the cations present around the colloidal particles also play a role of repelling cations present on surfaces of other colloidal particles, and dispersing the colloidal particles. When one surface of the hollow fiber membrane is brought into contact with an aqueous solution (a colloidal solution) that contains colloidal particles to circulate carbon dioxide gas to a side of the other surface, the colloidal solution and the carbon dioxide gas come into contact with each other via an opening portion of the hollow fiber membrane, and carbon dioxide ($CO_2$) is dissolved in water. Accordingly, bicarbonate ions ($HCO_3-$), carbonate ions ($CO_3^{2-}$), and hydrogen ions ($H+$) are generated in the colloidal solution, and thereby conductivity of the colloidal solution increases. In addition, the cations present around the colloidal particles are pushed close to the surfaces of the colloidal particles, and thereby a thickness of the electric double layer is reduced. As a result, the colloidal particles approach each other within a range in which intermolecular force works between the colloidal particles, and the colloidal particles become easy to aggregate with each other before repelling between the cations surrounding the particles occur. It is presumed that, as a result, other colloidal particles become easy to aggregate with the colloidal particles adsorbed on a surface of the hollow fiber membrane, and thereby a coating amount of the antithrombotic high-molecular compound is increased. Furthermore, it is perceived that a coating amount is also increased by adsorption of colloidal particles in an aggregated state in the colloidal solution onto the surface of the hollow fiber membrane. Accordingly, an artificial lung produced by the method according to the present disclosure has excellent antithrombotic properties.

Hereinafter, preferred embodiments of the present disclosure will be described. The present disclosure is not limited only to the following embodiments. Hereinafter, a hollow fiber membrane artificial lung of an outside blood flow type will be specifically described as the preferred embodiment, but an artificial lung produced by the method of the present disclosure may be a hollow fiber membrane artificial lung of an inside blood flow type, and even to this case, the present disclosure can be applied by appropriately changing the following embodiment. In addition, dimensional ratios of the drawings are exaggerated for convenience of explanation and may differ from actual ratios in some cases.

In the present specification, "X to Y" indicating a range includes X and Y, and means "X or more and Y or less." In addition, unless otherwise specified, operations, and measurements of physical properties or the like are performed under conditions of room temperature (20° C. to 25° C.)/ relative humidity of 40% RH to 50% RH.

Method for Producing Artificial Lung

A method for producing an artificial lung according to the present disclosure is a method for producing an artificial lung including a plurality of porous hollow fiber membranes for gas exchange which have an outer surface, an inner surface forming a lumen, and an opening portion communicating the outer surface with the inner surface. The method includes a step of bringing any of the outer surface and the inner surface into contact with a colloidal solution that contains an antithrombotic high-molecular compound to circulate carbon dioxide gas to a side of the other surface.

In the method of the present disclosure, first, a solution (a colloidal solution) containing a colloid of an antithrombotic high-molecular compound is prepared. In addition, the colloidal solution is brought into contact with any one of the outer surface and the inner surface of the hollow fiber membrane to circulate carbon dioxide gas to a side of the other surface. Hereinafter, the method will be described as (1) Preparation step of colloidal solution, and (2) Application (coating) step of colloidal solution.

(1) Preparation Step of Colloidal Solution

In the present step, the colloidal solution is prepared for application to the outer surface or the inner surface of the hollow fiber membrane. As described above, the colloidal solution used in the method according to the present disclosure has the antithrombotic high-molecular compound.

First, the antithrombotic high-molecular compound used in the preparation of the colloidal solution according to the present disclosure will be described.

Antithrombotic High-Molecular Compound and Method for Producing the Same

The antithrombotic high-molecular compound used in the present disclosure is a compound that is applied to the hollow fiber membrane to impart antithrombotic properties to an artificial lung.

The antithrombotic high-molecular compound can be used without particular limitation as long as it has the antithrombotic properties and biocompatibility. Among them, from the viewpoint of exhibiting the excellent characteristics mentioned above, the antithrombotic high-molecular compound preferably has a structural unit derived from an alkoxyalkyl (meth)acrylate represented by Formula (I):

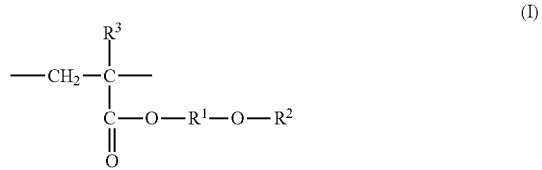

In Formula (I), R3 represents a hydrogen atom or methyl group, R1 represents an alkylene group having 1 carbon atoms to 4 carbon atoms, and R2 represents an alky group having 1 carbon atoms to 4 carbon atoms. The compound having the structural unit represented by Formula (I) has the excellent antithrombotic properties and biocompatibility (effects of suppressing and preventing adhesion and attachment of platelets, and effects of suppressing and preventing activation of platelets), and particularly has excellent effects of suppressing and preventing adhesion and attachment of platelets. Accordingly, by using the compound having the structural unit, it is possible to produce an artificial lung having the excellent antithrombotic properties and biocompatibility (effects of suppressing and preventing adhesion and attachment of platelets, and effects of suppressing and preventing activation of platelets), and particularly having excellent effects of suppressing and preventing adhesion and attachment of platelets.

In the present specification, "(meth)acrylate" means "acrylate and/or methacrylate." That is, "alkoxyalkyl (meth)acrylate" includes all cases of only alkoxyalkyl acrylate, only alkoxyalkyl methacrylate, and alkoxyalkyl acrylate and alkoxyalkyl methacrylate.

In Formula (I), R1 represents an alkylene group having 1 carbon atoms to 4 carbon atoms. The alkylene group having 1 carbon atoms to 4 carbon atoms is not particularly limited, and includes a linear or a branched alkylene group of a methylene group, an ethylene group, a trimethylene group, a tetramethylene group, and a propylene group. Among these, an ethylene group and a propylene group are preferable, and in consideration of further enhanced effects of antithrombotic activity and biocompatibility, an ethylene group is particularly preferable. R2 represents an alkyl group having 1 carbon atoms to 4 carbon atoms. The alkyl group having 1 carbon atoms to 4 carbon atoms is not particularly limited, and includes a linear or a branched alkyl group of a methyl group, an ethyl group, a propyl group, an isopropyl group, a butyl group, an isobutyl group, a sec-butyl group, and a tert-butyl group. Among these, a methyl group and an ethyl group are preferable, and in consideration of further enhanced effects of antithrombotic activity and biocompatibility, a methyl group is particularly preferable. R3 represents a hydrogen atom or a methyl group. In a case where the antithrombotic high-molecular compound according to the present disclosure has two or more of structural units derived from alkoxyalkyl (meth)acrylate, each structural unit may be the same or different from each other.

Specific examples of alkoxyalkyl (meth)acrylate include methoxymethyl acrylate, methoxyethyl acrylate, methoxypropyl acrylate, ethoxymethyl acrylate, ethoxyethyl acrylate, ethoxypropyl acrylate, ethoxybutyl acrylate, propoxymethyl acrylate, butoxyethyl acrylate, methoxybutyl acrylate, methoxymethyl methacrylate, methoxyethyl methacrylate, ethoxymethyl methacrylate, ethoxyethyl methacrylate, propoxymethyl methacrylate, butoxyethyl methacrylate, and the like. Among them, from the viewpoint of further enhanced effects of antithrombotic activity and biocompatibility, methoxyethyl (meth)acrylate and methoxybutyl acrylate are preferable, and methoxyethyl acrylate (MEA) is particularly preferable. That is, the antithrombotic high-molecular compound according to the present disclosure is preferably polymethoxyethyl acrylate (PMEA). The above alkoxyalkyl (meth)acrylate may be used alone or may be used by mixing two or more kinds of alkoxyalkyl (meth)acrylates.

The antithrombotic high-molecular compound according to the present disclosure preferably has a structural unit derived from alkoxyalkyl (meth)acrylate, and may be a polymer (homopolymer) consisting of one or two or more of structural units derived from alkoxyalkyl (meth)acrylate, or may be a polymer (copolymer) consisting of one or two or more of structural units derived from alkoxyalkyl (meth) acrylate, and consisting of one or two or more of structural units (other structural units) derived from a monomer copolymerizable with the alkoxyalkyl (meth)acrylate. In a case where the antithrombotic high-molecular compound according to the present disclosure consists of two or more of the structural units, the structure of the polymer (copolymer) is not particularly limited, and may be any one of a random copolymer, an alternating copolymer, a periodic copolymer, or a block copolymer. In addition, the end of the polymer is not particularly limited and is appropriately determined according to the type of raw material being used, but is generally a hydrogen atom.

In a case where the antithrombotic high-molecular compound according to the present disclosure has other structural units in addition to the structural units derived from alkoxyalkyl (meth)acrylate, a monomer copolymerizable with the alkoxyalkyl (meth)acrylate (copolymerizable monomer) is not particularly limited. Examples of the monomer copolymerizable with the alkoxyalkyl (meth)acrylate (copolymerizable monomer) can include methyl acrylate, ethyl acrylate, propyl acrylate, butyl acrylate, 2-ethylhexyl acrylate, methyl methacrylate, ethyl methacrylate, propyl methacrylate, butyl methacrylate, 2-ethylhexyl methacrylate, hexyl acrylate, hexyl methacrylate, ethylene, propylene, acrylamide, N,N-dimethylacrylamide, N,N-diethylacrylamide, aminomethyl acrylate, aminoethyl acrylate, aminoisopropyl acrylate, diaminomethyl acrylate, diaminoethyl acrylate, diaminobutyl acrylate, methacrylamide, N,N-dimethylmethacrylamide, N,N-diethyl methacrylamide, aminomethyl methacrylate, aminoethyl methacrylate, diaminomethyl methacrylate, diaminoethyl methacrylate, and the like. Among them, as a copolymerizable monomer, a monomer not having a hydroxyl group or a cationic group in the molecule is preferable. The copolymer may be any one of a random copolymer, a block copolymer, or a graft copolymer, and can be synthesized by a known method such as radical polymerization, ionic polymerization, and polymerization using a macromer. In all structural units of the copolymer, a ratio of the structural units derived from a copolymerizable monomer is not particularly limited, but in consideration of antithrombotic activity and biocompatibility, and the like, it is preferable that the structural units derived from a copolymerizable monomer (the other structural units) are more than 0% by mole and 50% by mole or less with respect to all structural units of the copolymer. When the units are more than 50% by mole, there is a possibility that the effect of alkoxyalkyl (meth)acrylate deteriorates.

A weight-average molecular weight of the antithrombotic high-molecular compound according to the present disclosure is not particularly limited, but is preferably 80,000 or more. In the method for producing an artificial lung according to the present disclosure, the antithrombotic high-molecular compound is applied to the outer surface or the inner surface of the hollow fiber membrane in a form of the colloidal solution. Accordingly, from the viewpoint of easily preparing a desired colloidal solution, a weight-average molecular weight of the antithrombotic high-molecular compound is preferably, for example, less than 800,000. When the weight-average molecular weight of the colloidal solution is within the above-mentioned range, it is possible to prepare a stable colloidal solution containing the antithrombotic high-molecular compound by suppressing aggregation or precipitation of the compound in the solution. In addition, a weight-average molecular weight of the antithrombotic high-molecular compound is preferably, for example, more than 200,000 and less than 800,000, is more preferably, for example, 210,000 to 600,000, is even more preferably, for example, 220,000 to 500,000, and is particularly preferably, for example, 230,000 to 450,000.

In the present specification, a "weight-average molecular weight" is a weight obtained by adopting a value measured by gel permeation chromatography (GPC) using polystyrene as a standard substance and tetrahydrofuran (THF) as a mobile phase, respectively. Specifically, a polymer to be analyzed is dissolved in THF to prepare a 10 mg/ml solution. Regarding the polymer solution prepared as above, GPC column LF-804 manufactured by Shodex is attached to a GPC system LC-20 manufactured by Shimadzu Corporation, THF is allowed to flow as a mobile phase, and polystyrene is used as a standard substance to measure GPC of the polymer to be analyzed. After preparing a calibration curve with a standard polystyrene, a weight-average molecular weight of the polymer to be analyzed is calculated based on this curve.

It is presumed that, by increasing a molecular weight of the antithrombotic high-molecular compound, it is possible to reduce a content of polymer with a relatively small molecular weight which is contained in a coating, and as a result, it is possible to obtain effects of suppressing and preventing the polymer with a relatively small molecular weight from eluting into blood. Accordingly, in a case where a weight-average molecular weight of the antithrombotic high-molecular compound is within the above-mentioned range, elution of the coating (particularly a polymer with a low molecular weight) into blood can be further effectively suppressed and prevented. In addition, this is also preferable in terms of the antithrombotic properties and the biocompatibility. Furthermore, in the present specification, the "polymer with a low molecular weight" means a polymer having a weight-average molecular weight, for example, of less than 60,000. A method for measuring a weight-average molecular weight is as described above.

In addition, the antithrombotic high-molecular compound containing the structural unit derived from alkoxyalkyl (meth)acrylate represented by Formula (I) can be produced by a well-known method. Specifically, the following method is preferably used.

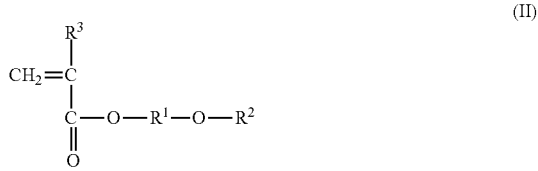

(II)

One or two or more monomers (copolymerizable monomer) copolymerizable with alkoxyalkyl (meth)acrylate represented by Formula (II) and with the above alkoxyalkyl (meth)acrylate that is added as necessary, are stirred in a polymerization solvent together with a polymerization initiator to prepare a monomer solution, and by heating the above monomer solution, alkoxyalkyl (meth)acrylate or alkoxyalkyl (meth)acrylate and a copolymerizable monomer that is added as necessary are (co)polymerized. In Formula (II), since substituents $R^1$, $R^2$, and $R^3$ are the same as those defined in Formula (I), explanation is omitted.

The polymerization solvent that can be used in the above preparation of the monomer solution is not particularly limited, as long as alkoxyalkyl (meth)acrylate of Formula (II) and a copolymerizable monomer that is added as necessary, which are being used, can be dissolved in the solvent. Examples of the polymerization solvent can include water, alcohols such as methanol, ethanol, propanol and isopropanol; aqueous solvents such as polyethylene glycols; aromatic solvents such as toluene, xylene and tetralin; halogenated solvents such as chloroform, dichloroethane, chlorobenzene, dichlorobenzene, trichlorobenzene; and the like. Among them, in consideration of alkoxyalkyl (meth)acrylate being easily dissolved and the polymer that has the above weight-average molecular weight being easily obtained, methanol is preferable.

A monomer concentration in the monomer solution is not particularly limited, but a weight-average molecular weight of the antithrombotic high-molecular compound obtained can be increased by setting the concentration relatively high. For this reason, in consideration of the polymer that has the above weight-average molecular weight being easily obtained, and the like, the monomer concentration in the monomer solution is preferably, for example, less than 50% by mass, and is more preferably, for example, 15% by mass or more and less than 50% by mass. In addition, the monomer concentration in the monomer solution is more preferably, for example, 20% by mass to 48% by mass, and is particularly preferably, for example, 25% by mass to 45% by mass. In a case of using two or more kinds of monomers, the above-mentioned monomer concentration means a total concentration of these monomers.

The polymerization initiator is not particularly limited and a known initiator may be used. The initiator is preferably a radical polymerization initiator in terms of being excellent in polymerization stability, and specific examples of the polymerization initiator can include persulfates such as potassium persulfate (KPS), sodium persulfate and ammonium persulfate; peroxides such as hydrogen peroxide, t-butyl peroxide and methyl ethyl ketone peroxide; and azo compounds such as azobisisobutyronitrile (AIBN), 2,2'-azobis(4-methoxy-2,4-dimethylvaleronitrile), 2,2'-azobis(2,4-dimethylvaleronitrile), 2,2'-azobis[2-(2-imidazolin-2-yl)propane]dihydrochloride, 2,2'-azobis[2-(2-imidazolin-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, α-cumyl peroxyneodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl) peroxydicarbonate, di(secondary butyl)peroxydicarbonate, and azobiscyanovaleric acid. In addition, for example, a reducing agent such as sodium sulfite, sodium hydrogen sulfite, and ascorbic acid may be used in combination with the above radical polymerization initiators as a redox type initiator. A blending amount of the polymerization initiator is, for example, 0.0001 mol % to 1 mol %, is more preferably, for example, 0.001 mol % to 0.8 mol %, and is particularly preferably, for example, 0.01 mol % to 0.5 mol %, with respect to a total amount of monomers (alkoxyalkyl (meth)acrylate and a copolymerizable monomer that is added as necessary; the same applies hereinafter). Alternatively, a blending amount of the polymerization initiators is preferably, for example, 0.005 parts by mass to 2 parts by mass, and is more preferably, for example, 0.05 parts by mass to 0.5 parts by mass with respect to 100 parts by mass of monomer (a total weight in a case of using a plurality types of monomers). With such a blending amount of the polymerization initiators, the polymer having a desired weight-average molecular weight can be efficiently produced.

The above polymerization initiator as it is may be mixed with the monomers and the polymerization solvent, or the initiator in a solution state obtained by the initiator dissolved in another solvent in advance as it is, may be mixed with the monomers and the polymerization solvent. In a latter case, the other solvent is not particularly limited, as long as the polymerization initiator can be dissolved in the solvent, and the same solvent as the above polymerization solvent can be exemplified. Furthermore, the other solvent may be the same as or different from the above polymerization solvent, but is preferably a solvent that is the same as the above polymerization solvent in consideration of the ease of control of polymerization, and the like. Furthermore, in this case, a concentration of the polymerization initiator in the other solvent is not particularly limited, but an addition amount of the polymerization initiator is preferably, for example, 0.1 parts by mass to 10 parts by mass, is more preferably, for example, 0.15 parts by mass to 5 parts by mass, and is even more preferably, for example, 0.2 parts by mass to 1.8 parts by mass with respect to 100 parts by mass of the other solvent in consideration of the ease of mixing, and the like.

Next, the above monomer solution is heated, and thus alkoxyalkyl (meth)acrylate or alkoxyalkyl (meth)acrylate and the other monomer are (co)polymerized. As a polymerization method, for example, a known polymerization method such as radical polymerization, anionic polymerization, and cationic polymerization can be adopted, and radical polymerization by which production is easy is preferably used.

A polymerization condition is not particularly limited, as long as the above monomers (alkoxyalkyl (meth)acrylate or alkoxyalkyl (meth)acrylate and the copolymerizable monomer) can be polymerized under the condition. Specifically, the polymerization temperature is preferably, for example, 30° C. to 60° C., and is more preferably, for example, 40° C. to 55° C. In addition, the polymerization time is preferably, for example, 1 hour to 24 hours, and is preferably, for example, 3 hours to 12 hours. Under such conditions described above, a polymer having a high molecular weight as above can be further efficiently produced. Furthermore, it is possible to effectively suppress and prevent gelation in the polymerization process and to achieve high production efficiency.

In addition, a chain transfer agent, a polymerization rate-adjusting agent, a surfactant, and other additives may be appropriately used during polymerization if necessary.

An atmosphere under which the polymerization reaction is carried out is not particularly limited, and the reaction may be carried out under an air atmosphere, an inert gas atmosphere such as nitrogen gas or argon gas, and the like. In addition, during the polymerization reaction, the reaction solution may be stirred.

The polymer after polymerization can be purified by a general purification method such as a re-precipitation method, a dialysis method, an ultrafiltration method, and an extraction method. Among them, it is preferable to carry out purification by the re-precipitation method, because a (co)polymer suitable for preparation of the colloidal solution can be obtained. In this case, it is preferable to use ethanol as a poor solvent used to perform re-precipitation.

The purified polymer can be dried by an arbitrary method such as freeze drying, reduced pressure drying, spray drying, and heat drying, but freeze drying or reduced pressure drying is preferable from the viewpoint that the influence on the physical properties of the polymer is small.

Next, a method for preparing the colloidal solution according to the present disclosure will be described.

Preparation of Colloidal Solution

A solvent used for preparation of the solution (the colloidal solution) containing the antithrombotic high-molecular compound is not particularly limited as long as it is a solvent in which the antithrombotic high-molecular compound is appropriately dispersed to prepare a colloidal solution. The solvent preferably contains water from the viewpoint of further effectively preventing infiltration of the colloidal solution to the outer surface or the inner surface (surfaces on a side where oxygen-containing gas flows) of fine pores of the hollow fiber membranes. Water is preferably pure water, ion exchange water, or distilled water, and is particularly preferably distilled water.

In addition, a solvent, which is used in preparation of the colloidal solution and which is other than water, is not particularly limited, but is preferably methanol or acetone in consideration of easiness of controlling dispersibility and the like of the antithrombotic high-molecular compound. The above-mentioned solvent other than water may be used alone or in a form of a mixture of two or more kinds of solvents. Among these, the solvent is preferably methanol in consideration of further easiness of controlling dispersibility and the like of the antithrombotic high-molecular compound. In other words, the solvent is preferably composed of water and methanol. A mixing ratio of water and methanol is not particularly limited, but in consideration of further easiness of controlling dispersibility of the antithrombotic high-molecular compound and average particle diameter of a colloid, the mixing ratio (a mass ratio) of water:methanol is preferably, for example, 6:1 to 32:1, and is more preferably, for example, 10:1 to 25:1. In other words, the solvent is preferably composed of water and methanol at a mixing ratio (a mass ratio) of, for example, 6:1 to 32:1, and is more preferably composed of water and methanol at a mixing ratio (a mass ratio) of, for example, 10:1 to 25:1.

As described above, when preparing the colloidal solution using a mixed solvent of water and a solvent other than water, the order in which the solvent (for example, water and methanol) and the antithrombotic high-molecular compound are added is not particularly limited, but it is preferable to prepare the colloidal solution according to the following procedure. In other words, it is preferable to prepare the colloidal solution by a method in which the antithrombotic high-molecular compound is added to a solvent other than water (preferably methanol) to prepare a solution containing the antithrombotic high-molecular compound, and subsequently, the solution containing the antithrombotic high-molecular compound is added to water. According to such a method, the antithrombotic high-molecular compound is easily dispersed. In addition, according to the above-mentioned method, there is also an advantage that a colloid having a uniform particle diameter can be formed, and a uniform coating can be easily formed.

In the above-mentioned method, an addition rate for the solution containing the antithrombotic high-molecular compound to water is not particularly limited, but it is preferable to add the solution containing the antithrombotic high-molecular compound to water at a rate of, for example, 5 g/m in to 100 g/m in.

A stirring time and a stirring temperature at the time of preparing the colloidal solution are not particularly limited, but from the viewpoint that a colloid having a uniform particle diameter can be easily formed and the colloid can be dispersed uniformly, it is preferable to perform stirring, for example, for 1 minute to 30 minutes, and it is more preferable to perform stirring, for example, for 5 minutes to 15 minutes after addition of the solution containing the antithrombotic high-molecular compound to water. In addition, a stirring temperature is preferably, for example, 10° C. to 40° C., and is more preferably, for example, 20° C. to 30° C.

A concentration of the antithrombotic high-molecular compound in the colloidal solution is not particularly limited, but is preferably, for example, 0.01% by mass or more from the viewpoint of easily increasing the coating amount. In addition, from the above-described viewpoint, the colloidal solution preferably contains the antithrombotic high-molecular compound at a concentration of, for example, 0.05% by mass or more, and particularly preferably contains the antithrombotic high-molecular compound at a concentration of, for example, 0.1% A by mass or more. Meanwhile, an upper limit of the concentration of the antithrombotic high-molecular compound in the colloidal solution is not particularly limited, but is preferably, for example, 0.3% by mass or less, and is more preferably, for example, 0.2% by mass or less, in consideration of easiness of forming the coating, an effect of reducing coating unevenness, and the like. In addition, when the upper limit is within such a range, a deterioration in a gas exchange capacity due to an excessively thick coating of the antithrombotic high-molecular compound is suppressed.

(2) Application (Coating) Step of Colloidal Solution

Figure 3:
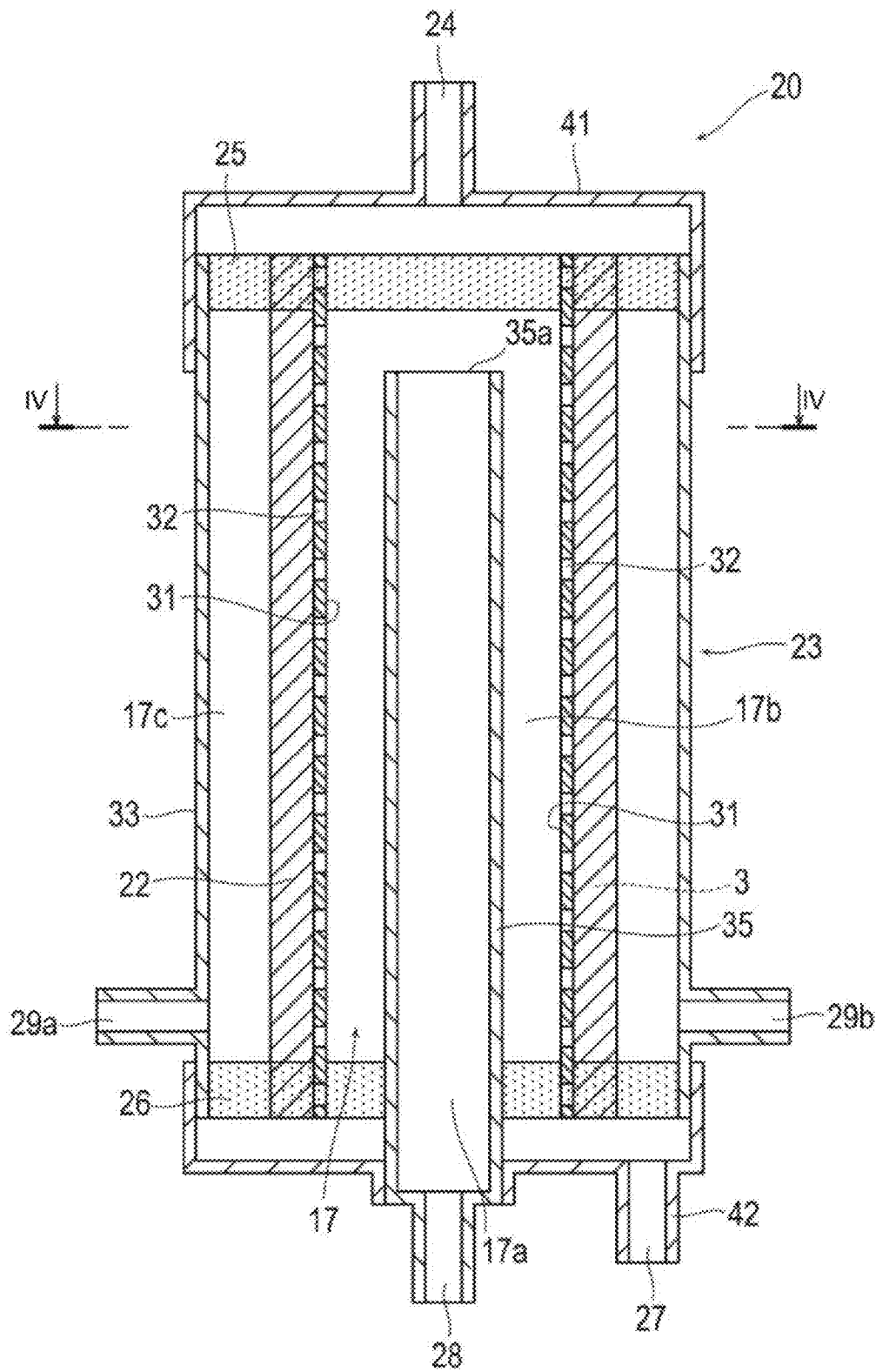
FIG. 3 is a cross-sectional view showing another embodiment of the hollow fiber membrane artificial lung of an outside blood flow type according to the present disclosure.

Next, the colloidal solution prepared as described above is applied (coated) to the outer surface or the inner surface of the hollow fiber membrane. Specifically, the outer surface or the inner surface (that is, a blood contact portion) of the hollow fiber membrane is coated with the antithrombotic high-molecular compound by assembling an artificial lung (for example, an artificial lung having a structure as shown in FIG. 1 or FIG. 3 which will be described later), and thereafter, bringing the colloidal solution prepared in the above step (1) into contact with (or circulating to) any one of the outer surface or the inner surface of the hollow fiber membrane to circulate carbon dioxide gas to the side of the other surface. Accordingly, a coating film containing the antithrombotic high-molecular compound is formed on the outer surface or the inner surface of the hollow fiber membrane. In addition, application of the colloidal solution to the hollow fiber membrane may be carried out before assembling the artificial lung as long as the colloidal solution is brought into contact with (or circulated to) any one of the outer surface or the inner surface of the hollow fiber membrane to circulate carbon dioxide gas to the side of the other surface.

A preferred embodiment of the artificial lung produced by the method according to the present disclosure is an artificial lung of an outside flow type, which is an embodiment in which the outer surface of the hollow fiber membrane is coated with the antithrombotic high-molecular compound. Accordingly, in the present step, it is preferable to apply the colloidal solution to the outer surface of the hollow fiber membrane in order to produce an artificial lung having the above-described configuration. In other words, the production method according to the present disclosure is preferably a method in which, in the application (coating) step of the colloidal solution, the outer surface is brought into contact with the colloidal solution containing the antithrombotic high-molecular compound and circulating carbon dioxide gas to the side of the inner surface.

In addition, a method for bringing any one of the outer surface and the inner surface of the hollow fiber membrane into contact with the colloidal solution containing the antithrombotic high-molecular compound is not particularly limited, but any suitable method for use as an artificial lung, such as filling and dip coating (an immersion method) can be applied. Among them, for an increase in the coating amount of the antithrombotic high-molecular compound, the filling is preferable.

In addition, in a state where any one of the outer surface and the inner surface is brought into contact with the colloidal solution containing the antithrombotic high-molecular compound, carbon dioxide gas is circulated to the side of the other surface. Accordingly, the colloidal solution and carbon dioxide gas comes into contact with each other via the opening portion of the hollow fiber membrane, carbon dioxide dissolves in the colloidal solution, aggregation and adsorption of colloidal particles to the surface of the hollow fiber membrane are perceived to progress by the aforementioned mechanism.

A circulation amount of carbon dioxide gas in this case is not particularly limited, but is preferably, for example, 50 mL to 5000 mL, and is more preferably, for example, 100 mL to 3000 mL with respect to 1 g of the colloidal solution. When a circulation amount of carbon dioxide gas is, for example, 50 mL or more per 1 g of the colloidal solution, a sufficient amount of carbon dioxide is dissolved in the colloidal solution, and a thickness of the electric double layer of the colloidal particles is reduced, and thereby aggregation and adsorption of the colloidal particles to the surface of the hollow fiber membrane are perceived to proceed favorably. As a result, it is possible to obtain an artificial lung coated with a sufficient amount of the antithrombotic high-molecular compound. On the other hand, when a circulation amount of carbon dioxide gas is, for example, 5000 mL or less per 1 g of the colloidal solution, an amount of colloidal particles adsorbed on the surface of the hollow fiber membrane does not become excessively large, and it is possible to prevent the gas exchange capacity from being lowered. In the present specification, a volume (L) of carbon dioxide gas means a volume, for example, at 25° C. and 1 atm.

When the carbon dioxide gas is circulated, in addition to the carbon dioxide gas, another gas (for example, an inert gas such as a nitrogen gas) may be circulated. From the viewpoint of obtaining an artificial lung with a sufficient coating amount and little coating unevenness, a proportion of the other gas is preferably smaller than that of carbon dioxide gas. Specifically, a circulation amount (a volume) of the other gas is preferably, for example, 0% by volume to 50% by volume, and is more preferably, for example, 0% by volume to 20% by volume, and is most preferably, for example, 0% by volume, with respect to a circulation amount (a volume) of carbon dioxide gas.

In a case where filling is adopted as the method for bringing any one of the outer surface and the inner surface of the hollow fiber membrane into contact with the colloidal solution containing the antithrombotic high-molecular compound, a filling amount of the colloidal solution is preferably, for example, 50 g/m$^2$ or more, and is more preferably, for example, 80 g/m$^2$ or more, with respect to the membrane area (m$^2$) of the hollow fiber membrane. When a filling amount is, for example, 50 g/m$^2$ or more, the coating containing a sufficient amount of the antithrombotic high-molecular compound can be formed on the surface of the hollow fiber membrane. Meanwhile, an upper limit value of the filling amount is not particularly limited, but is preferably, for example, 200 g/m$^2$ or less, and is more preferably, for example, 150 g/m$^2$ or less.

In the present specification, the term "membrane area" refers to an area of the outer surface or an area of the inner surface of the hollow fiber membrane. In a case where the outer surface of the hollow fiber membrane is coated with the antithrombotic high-molecular compound (that is, in a case where the artificial lung is the hollow fiber membrane artificial lung of an outside blood flow type), the "membrane area" refers to an area of the outer surface of the hollow fiber membrane, and is calculated from a product of an outer diameter, a circumference ratio, the number, and an effective length of the hollow fiber membrane. On the other hand, in a case where the inner surface of the hollow fiber membrane is coated with the antithrombotic high-molecular compound (that is, in a case where the artificial lung is the hollow fiber membrane artificial lung of an inside blood flow type), the "membrane area" refers to an area of the inner surface of the hollow fiber membrane, and is calculated from a product of an inner diameter, a circumference ratio, the number, and an effective length of the hollow fiber membrane.

A flow rate of carbon dioxide gas is not particularly limited, but is preferably, for example, 1 L/min·m$^2$ to 20 L/min·m$^2$, and is preferably, for example, 2 L/min·m$^2$ to 10 L/min·m$^2$ with respect to the membrane area (m$^2$) of the hollow fiber membrane. By circulating carbon dioxide gas at the above-mentioned rate, aggregation and adsorption of colloidal particles to the surface of the hollow fiber membrane proceed favorably, and it is possible to obtain an artificial lung with a sufficient coating amount and little coating unevenness.

In addition, a flow time of carbon dioxide gas is not particularly limited, but is preferably, for example, 1 minute to 100 minutes, and is more preferably, for example, 2 minutes to 70 minutes in consideration of a coating amount, easiness of forming a coating film, an effect of reducing coating unevenness, and the like. Furthermore, a contact temperature of the colloidal solution and the hollow fiber membranes (a circulation temperature of the colloidal solution to a blood flowing side of the artificial lung) is preferably, for example, 5° C. to 40° C., and is more preferably, for example, 15° C. to 30° C. in consideration of a coating amount, easiness of forming a coating film, an effect of reducing coating unevenness, and the like. When contact of the colloidal solution and the hollow fiber membranes, the colloidal solution is preferably allowed to stand.

By drying the coating film after contact with the colloidal solution, the coating by the antithrombotic high-molecular compound according to the present disclosure is formed on the outer surface or the inner surface of the hollow fiber membrane. A drying condition is not particularly limited as long as it is a condition where the coating by the antithrombotic high-molecular compound according to the present disclosure can be formed on the outer surface (furthermore, on an outer surface layer) or on the inner surface (furthermore, on an inner surface layer) of the hollow fiber membrane. Specifically, a drying temperature is preferably, for example, 5° C. to 50° C., and more preferably, for example, 15° C. to 40° C. In addition, drying time is preferably, for example, 60 minutes to 300 minutes, and more preferably, for example, 120 minutes to 240 minutes. Alternatively, the coating film may be dried by allowing a gas to continuously or gradually flow into the hollow fiber membranes, the gas preferably being, for example, 5° C. to 40° C., and more preferably, for example, 15° C. to 30° C. The types of the gas are not particularly limited as long as a gas has no influence on the coating film and the coating film can be dried thereby. Specific examples of the gas can include air, inert gas such as nitrogen gas, argon gas, and the like. As long as the coating film can be sufficiently dried with a circulation amount of the gas, an amount of the coating film is not particularly limited, but is preferably, for example, 5 L to 150 L, and more preferably, for example, 30 L to 100 L.

Artificial Lung

According to the method for producing an artificial lung according to the present disclosure, the coating containing a sufficient amount of the antithrombotic high-molecular compound can be formed on the outer surface or the inner surface of the hollow fiber membrane. In other words, according to one aspect of the present disclosure, there is provided the artificial lung including a plurality of porous hollow fiber membranes for gas exchange which have the outer surface, the inner surface forming a lumen, and the opening portion communicating the outer surface with the inner surface, in which any one of the outer surface and the inner surface has a coating in which the antithrombotic high-molecular compound is contained in an amount of, for example, 10 mg/m$^2$ surface to 100 mg/m$^2$ surface. An amount of the antithrombotic high-molecular compound in the coating is more preferably, for example, 15 mg/m$^2$ surface to 60 mg/m$^2$ surface. When a coating amount of the antithrombotic high-molecular compound is, for example, 10 mg/m$^2$ surface or more, an artificial lung having the excellent antithrombotic properties is obtained. Meanwhile, an upper limit of the coating amount is not particularly limited, but is preferably, for example, 100 mg/m² or less. With such a coating amount, a deterioration in the gas exchange capacity due to an excessively thick coating of the antithrombotic high-molecular compound is suppressed, and thereby an artificial lung having the excellent gas exchange capacity is obtained. As the above-mentioned coating amount, values measured by a method to be described in the following examples are adopted.

For the same reason as described in the aforementioned method for producing an artificial lung according to the present disclosure, the artificial lung according to the present disclosure preferably has the above-mentioned coating on the outer surface of the hollow fiber membrane. In addition, a preferable chemical structure and a weight-average molecular weight of the antithrombotic high-molecular compound are also the same as those described in the aforementioned method for producing an artificial lung according to the present disclosure, and thus detailed description of antithrombotic high-molecular compound will be omitted.

In the artificial lung according to the present disclosure, as described above, since a sufficient amount of the antithrombotic high-polymer material is coated, the antithrombotic properties on the outer surface side or the inner surface side of the hollow fiber membrane are improved. Accordingly, when the artificial lung is incorporated into an extracorporeal circulation circuit to circulate blood, a maintenance rate of the number of platelets can be improved. Specifically, a maintenance rate of the number of platelets after circulating blood, for example, for 30 minutes is preferably more than 70%, is more preferably, for example, 80% or more, and is particularly preferably, for example, 90% or more (an upper limit: 100%). As the above-mentioned maintenance rate of the number of platelets, values measured by a method to be described in the following examples are adopted.

The details of the artificial lung according to the present disclosure will be described below with reference to the drawings.

Figure 2:
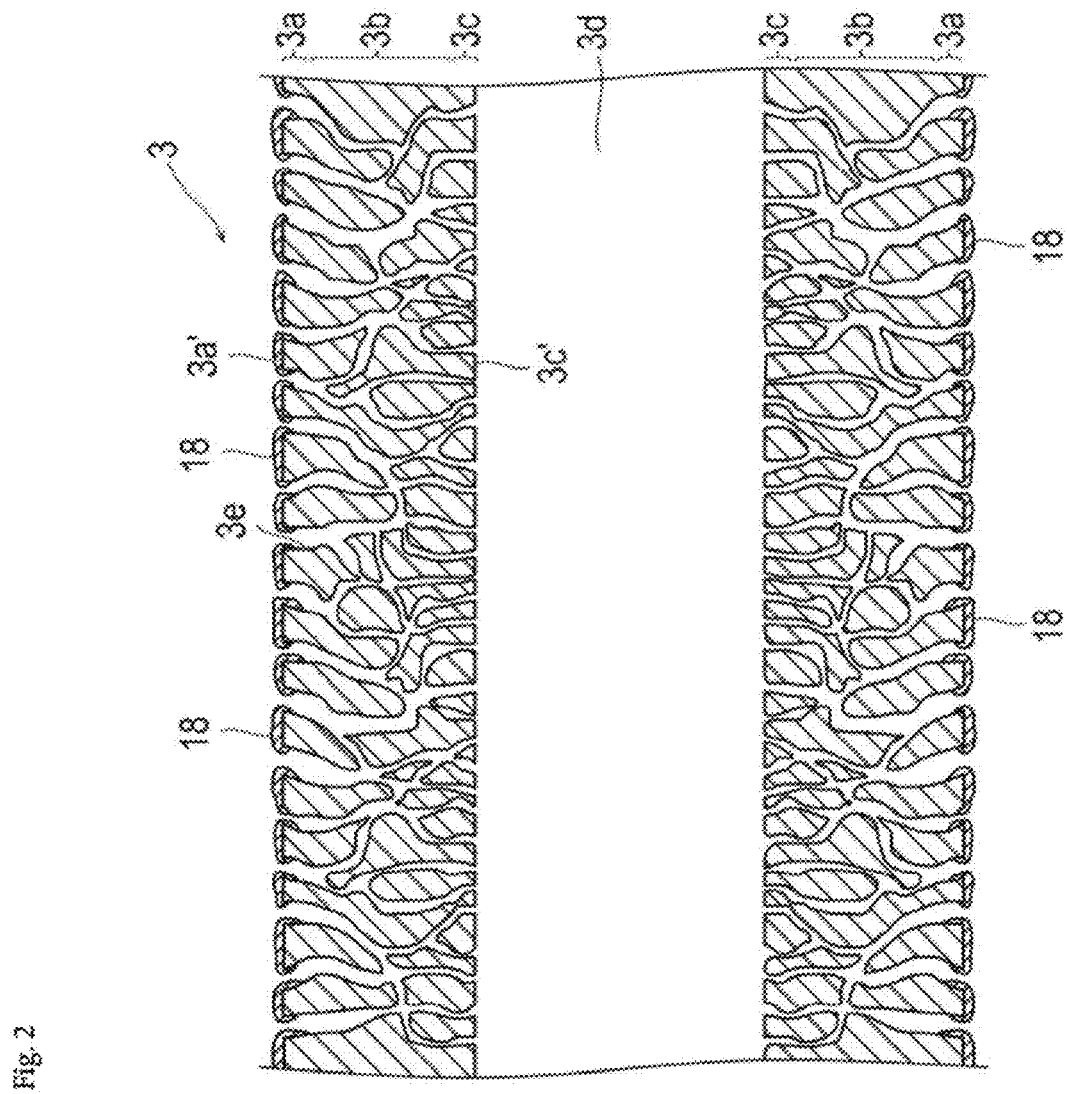
FIG. 2 is an enlarged cross-sectional view of a hollow fiber membrane used for the hollow fiber membrane artificial lung of an outside blood flow type according to the present disclosure.

FIG. 1 is a cross-sectional view of one embodiment of the hollow fiber membrane artificial lung of an outside blood flow type according to the present disclosure. FIG. 2 is an enlarged cross-sectional view of the porous hollow fiber membranes for gas exchange used for the hollow fiber membrane artificial lung of an outside blood flow type according to the present disclosure. FIG. 3 is a cross-sectional view of another embodiment of the artificial lung according to the present disclosure.

In FIG. 1, an artificial lung 1 is an artificial lung of a type in which a plurality of porous hollow fiber membranes 3 for gas exchange are accommodated in a housing 2, blood flows into the outer side of the hollow fiber membranes 3, and an oxygen-containing gas flows to the inside of the hollow fiber membranes 3. In FIG. 2, an antithrombotic high-molecular compound (i.e., antithrombotic material) 18 is coated on an outer surface of the hollow fiber membranes 3 which is a blood contact portion (an outer surface 3$a'$, or the outer surface 3$a'$ and an outer surface layer 3$a$). A coat (coating) of the antithrombotic high-molecular compound 18 is selectively formed on the outer surface 3$a'$ of the hollow fiber membrane 3. FIG. 2 shows an aspect in which the coat (coating) of the antithrombotic high-molecular compound 18 is formed on the outer surface 3$a'$ of the hollow fiber membranes used in the hollow fiber membrane artificial lung of an outside blood flow type. In the hollow fiber membranes of such an aspect, blood comes into contact with the outer surface 3$a'$ side, and the oxygen-containing gas circulates (i.e., flows) into an inner surface 3$c'$ side. The present disclosure may be applied to a hollow fiber membrane artificial lung of an inside blood flow type as described above. Accordingly, the hollow fiber membranes may have a reversed configuration with respect to the above aspect, that is, an aspect in which the coat (coating) of the antithrombotic high-molecular compound 18 is formed on the inner surface 3$c'$.

In the present specification, the sentence "the antithrombotic high-molecular compound coats the outside surface of the hollow fiber membrane" means that the coat (coating) of the antithrombotic high-molecular compound is formed on the outer surface of the hollow fiber membranes (a surface on the side where the blood flows) or on the outer surface and the outer surface layer. Meanwhile, in the present specification, the sentence "the antithrombotic high-molecular compound coats the outer surface of the hollow fiber membrane" means that the coat (coating) of the antithrombotic high-molecular compound is formed on the outer surface of the hollow fiber membranes (a surface on the side where the blood flows). In addition, "the antithrombotic high-molecular compound coats the outer surface layer of the hollow fiber membrane" means that the antithrombotic high-molecular compound penetrates into a part of the outer surface layer of the hollow fiber membranes (vicinity of the outer surface of the fine holes) to form the coat (coating). The coat (coating) of the antithrombotic high-molecular compound according to the present disclosure may be formed on at least a part of the blood contact portion of the hollow fiber membranes (outer surface), but it is preferable, for example, that the coat is formed on the entire blood contact portion of the hollow fiber membranes (outer surface) from the viewpoint of the antithrombotic activity and biocompatibility (the suppression and prevention effects of adhesion and attachment of the platelets and the suppression and prevention effects of activation of the platelets). In accordance with one aspect, the antithrombotic high-molecular compound preferably, for example, coats the entire blood contact portion of the artificial lung (outer surface).

In the embodiment according to FIG. 2, the antithrombotic high-molecular compound may exist on an internal layer 3$b$ or an inner surface layer 3$c$ of the hollow fiber membranes 3, but it is preferable, for example, that no substantial polymer exists on the internal layer 3$b$ or the inner surface layer 3$c$ of the hollow fiber membranes 3. In the present specification, "no substantial antithrombotic high-molecular compound exists on the internal layer 3$b$ or the inner surface layer 3$c$ of the hollow fiber membranes 3" means that the infiltration of the antithrombotic high-molecular compound was not observed in the vicinity of the inside surface of the hollow fiber membranes (a surface on the side where the oxygen-containing gas flows). In the method for producing an artificial lung according to the present disclosure, the coating is formed by applying the colloidal solution of an antithrombotic polymer, so that substantially no antithrombotic high-molecular compound may be provided in an inner surface layer 3$b$ or an inner surface layer 3$c$ of the hollow fiber membrane 3.

A hollow fiber membrane type artificial lung 1 includes a housing 2 having a blood inlet port 6 and a blood outlet port 7, a hollow fiber membrane bundle having a large number of porous hollow fiber membranes 3 for gas exchange accommodated in the housing 2. A pair of partition walls 4 and 5 liquid-tightly support both end portions of the hollow fiber membrane bundle within the housing 2. A blood chamber 12 is formed between the inside surface of the housing 2 and the partition walls 4 and 5, and the outside surfaces of the hollow fiber membranes 3. A gas chamber is formed inside the hollow fiber membranes 3, and a gas inlet port 8 and a gas outlet port 9 communicate with the gas chamber.

The hollow fiber membrane type artificial lung 1 of the present embodiment includes the tubular housing 2, an aggregate of the hollow fiber membranes 3 for gas exchange accommodated in the tubular housing 2, and the partition walls 4 and 5 liquid-tightly retaining both end portions of the hollow fiber membranes 3 within the housing 2. The tubular housing 2 is partitioned into the blood chamber 12 that is a first fluid chamber and the gas chamber that is a second fluid chamber. The blood inlet port 6 and the blood outlet port 7 communicating with the blood chamber 12 are provided in the tubular housing 2.

A cap-like gas inlet side header 10 having the gas inlet port 8 that is a second fluid inlet port communicating with the gas chamber that is the inner spaces of the hollow fiber membranes 3, is attached above the partition walls 4 that are the end portion of the tubular housing 2. A gas inlet chamber 13 is formed of the outside surface of the partition walls 4 and the inside surface of the gas inlet side header 10. The gas inlet chamber 13 communicates with the gas chamber that is formed of the inner spaces of the hollow fiber membranes 3.

A cap-like gas outlet side header 11 having a gas outlet port 9 that is a second fluid outlet port communicating with the inner spaces of the hollow fiber membranes 3, is attached below the partition walls 5. Aa gas outlet chamber 14 is formed of the outside surface of the partition walls 5 and the inside surface of the gas outlet side header 11.

The hollow fiber membranes 3 are porous membranes made of a hydrophobic polymer material. Membranes suitable for use as hollow fiber membranes in an artificial lung can be used and are not particularly limited. The hollow fiber membranes (for example, the inside surfaces of the hollow fiber membranes) are made of a hydrophobic polymer material, and thus the leakage of blood plasma components can be suppressed.

An inner diameter of the hollow fiber membrane is not particularly limited, but is preferably, for example, 50 µm to 300 µm. An outer diameter of the hollow fiber membrane is not particularly limited, but is preferably, for example, 100 µm to 400 µm. A wall thickness (a membrane thickness) of the hollow fiber membrane is preferably, for example, 20 µm to 100 µm, is more preferably, for example, 25 µm to 80 µm, is even more preferably, for example, 25 µm to 70 µm, and is particularly preferably, for example, 25 µm to 60 µm. In the present specification, a "wall thickness of the hollow fiber membrane (a membrane thickness)" means a wall thickness between the inner surface and the outer surface of the hollow fiber membrane, and is calculated by using the equation: [(outer diameter of hollow fiber membrane)−(inner diameter of hollow fiber membrane)]/2. For example, by setting a lower limit of the wall thickness of the hollow fiber membrane as described above, it is possible to secure sufficient strength of the hollow fiber membranes. Furthermore, it is satisfactory in terms of labor and cost in manufacturing, and is also preferable from the viewpoint of mass production. Furthermore, porosity of the hollow fiber membrane is preferably, for example, 5% by volume to 90% by volume, is more preferably, for example, 10% by volume to 80% by volume, and is particularly preferably, for example, 30% by volume to 60% by volume. A pore diameter of the hollow fiber membrane (that is, a pore diameter of the opening portion of the hollow fiber) is preferably, for example, 10 nm to 5 µm, is more preferably, for example, 50 nm to 1 µm, and is particularly preferably, for example, 50 nm to 100 nm.

In the present specification, a "diameter of the opening portion of the hollow fiber membrane" means an average diameter of the opening portions (in the present specification, will be simply referred to as a "pore") on a side coated with the antithrombotic high-molecular compound (the outer surface side in the present embodiment). In addition, an average diameter of the opening portions (in the present specification, will be simply referred to as a "pore diameter" or a "pore diameter") is measured by the method described below.

First, a SEM image of a side (for example, in the present embodiment, the outer surface) to be coated with the antithrombotic high-molecular compound is photographed for the hollow fiber membrane with a scanning electron microscope (SEM). Next, image processing is performed on the obtained SEM image, and the hole portion (opening portion) is inverted to white, the other is inverted to black, and the number of pixels in the white portion is measured. A boundary level of binarization is a value intermediate between the difference between the whitest part and the blackest part.

Subsequently, the number of pixels of the holes (opening portions) displayed in white is measured. An area of a hole can be calculated based on the number of pixels of each hole and the resolution (µm/pixel) of the SEM image thus determined. From the obtained hole area, a diameter of each hole is calculated by regarding the holes as a circle, and a statistically significant number, for example, diameters of 500 holes is randomly extracted, and an arithmetic mean of the diameter is used as a "an average diameter (i.e., diameter) of the opening portion of the hollow fiber."

As a material used for the porous membranes, for example, any suitable material used as the hollow fiber membranes in an artificial lung can be used. For example, there are a polyolefin resin such as polypropylene and polyethylene, a hydrophobic polymer material such as polysulfone, polyacrylonitrile, polytetrafluoroethylene, and cellulose acetate, and the like. Among these, a polyolefin resin, for example, is preferably used, and polypropylene, for example, is more preferable. The method for manufacturing hollow fiber membranes is not particularly limited, and any suitable method for manufacturing hollow fiber membranes can be applied in the same manner or in the manner of being appropriately modified. For example, it is preferable that micro fine holes are formed on the walls of the hollow fiber membranes through a stretching method or a solid-liquid phase separation method.

As a material constituting the tubular housing 2, for example, any material suitable for use as a material used for a housing of an artificial lung can be used. For example, there is a hydrophobic synthetic resin such as polycarbonate, acrylic-styrene copolymer, and acrylic-butylene-styrene copolymer. A shape of the housing 2 is not particularly limited, but is preferably cylindrical and transparent, for example. The inside of the housing 2 can be easily confirmed by forming the housing to be transparent.

An accommodation amount of the hollow fiber membranes of the present embodiment is not particularly limited, and any amount suitable for use in an artificial lung can be applied. For example, about 5,000 porous hollow fiber membranes 3 to 100,000 porous hollow fiber membranes 3 are accommodated in parallel in the housing 2 in an axial direction of the housing 2. Furthermore, in an exemplary embodiment, both the ends of the hollow fiber membranes 3 are respectively open towards both the ends of the housing 2, and the hollow fiber membranes 3 are fixed in a liquid-tight state by the partition walls 4 and 5. The partition walls 4 and 5 are formed by a potting agent such as polyurethane and silicone rubber. A portion interposed between the above partition walls 4 and 5 in the housing 2 is divided into the gas chamber inside the hollow fiber membranes 3 and the blood chamber 12 outside the hollow fiber membranes 3.

In the present embodiment, the gas inlet side header 10 having the gas inlet port 8 and the gas outlet side header 11 having the gas outlet port 9 are liquid-tightly attached to the housing 2. These headers may be formed of any material, and can be formed of a hydrophobic synthetic resin used for the housing described above, for example. The header may be attached by any method. For example, the header can be attached to the housing 2 by fusion bonding using ultrasound waves, high frequency waves, induction heating, and the like, by adhesion with an adhesive, or by mechanical engagement. In addition, the attachment may be performed by using a fastening ring (not shown). It is preferable that the entire blood contact portion of the hollow fiber membrane type artificial lung 1 (the inside surface of the housing 2, the outside surfaces of the hollow fiber membranes 3) is formed of a hydrophobic material.

As shown in FIG. 2, the antithrombotic high-molecular compound (i.e., material) 18 according to the present disclosure coats at least the outer surface 3a' (and optionally, the outer surface layer 3a depending on the cases, hereinafter the same applies) of the hollow fiber membranes 3 which becomes the blood contact portion of the hollow fiber membrane type artificial lung 1. As described above, it is preferable, for example, that no substantial antithrombotic high-molecular compound exists on the internal layer 3b or the inner surface layer 3c of the hollow fiber membranes. In the case, for example, since substantially no antithrombotic high-molecular compound exists, the hydrophobic properties of the base material itself of the membrane are maintained as they are on the internal layer 3b or the inner surface layer 3c of the hollow fiber membranes, and therefore the leakage of blood plasma components (leakage) can be effectively prevented. It is particularly preferable, for example, that no substantial antithrombotic high-molecular compound exist on both of the internal layer 3b or the inner surface layer 3c of the hollow fiber membranes. Furthermore, the hollow fiber membranes 3 include, in the center, a passage (lumen) 3d forming the gas chamber. In addition, the hollow fiber membranes 3 include an opening portion 3e through which the outer surface 3a' of the opening portion 3e and the inner surface 3c' communicate. The hollow fiber membranes having such a configuration are used in a state where the blood comes into the contact with outer surface 3a' side coated with the antithrombotic high-molecular compound 18, and meanwhile, the oxygen-containing gas flows into the inner surface 3c' side. In one exemplary embodiment utilizing an outside flow type artificial lung, the hollow fiber membranes 3 include the inner surface 3c' forming the lumen where the oxygen-containing gas flows, and the outer surface 3a' in contact with the blood, and the outer surface 3a' is coated with the coat containing the antithrombotic high-molecular compound.

In accordance with an exemplary embodiment, a coat (coating) of the antithrombotic high-molecular compound is selectively formed on the outer surface of the hollow fiber membrane (an outside flow type). For this reason, the blood (particularly blood plasma components) is unlikely to or does not infiltrate into the inside of the fine holes of the hollow fiber membranes. Therefore, it is possible to effectively help suppress or prevent blood (particularly blood plasma components) leakage from the hollow fiber membranes. Particularly, in a case where no substantial antithrombotic high-molecular compound exists on the internal layer 3b of the hollow fiber membranes and the inner surface layer 3c of the hollow fiber membranes, the hydrophobic state of the material is maintained on the internal layer 3b of the hollow fiber membranes and the inner surface layer 3c of the hollow fiber membranes, and therefore a large amount of blood (for example, blood plasma components) leakage (leakage) can be further help effectively suppressed or prevented. Accordingly, in the exemplary artificial lung obtained by the method of the present disclosure, a high level of gas exchange capacity can be maintained for a relatively long period of time.

In addition, according to the present disclosure, by using the colloidal solution, the coat (coating) of the antithrombotic high-molecular compound can be uniformly formed on the outer surface or the inner surface of the hollow fiber membrane. For example, adhesion and attachment, and activation of the platelets can be reduced on the blood contact portion of the hollow fiber membranes. Furthermore, separation of the coat from the hollow fiber membranes can be suppressed or prevented.

For example, the coat of the antithrombotic high-molecular compound according to the present embodiment is formed on the outer surface of the hollow fiber membranes of the artificial lung. In accordance with an exemplary embodiment, the coating may be formed on another constituent member (for example, on the entire blood contact portion) in addition to the outer surface. Adhesion, attachment, and activation of the platelets can be further effectively suppressed or prevented in the entire blood contact portion of the artificial lung. In addition, since a contact angle of the blood contact surface decreases, this can facilitate a priming operation. In an exemplary embodiment, the coat of the antithrombotic high-molecular compound can be formed on the other constituent member in contact with the blood. For example, the antithrombotic high-molecular compound does not coat a portion other than the blood contact portion of the hollow fiber membranes, or another portion of the hollow fiber membranes (for example, a portion buried in the partition walls). Such a portion is not in contact with the blood, and therefore the antithrombotic high-molecular compound not being coated thereon does not cause a particular problem.

In addition, the artificial lung obtained by the method of the present disclosure may be a type shown in FIG. 3. FIG. 3 is a cross-sectional view showing another embodiment of the artificial lung obtained by the method of the present disclosure. Furthermore, FIG. 4 is a cross-sectional view taken along line IV-IV of FIG. 3.

In FIG. 3, an artificial lung 20 (hollow fiber membrane artificial lung of an outside blood flow type) includes an inner tubular member 31 having a blood circulation opening 32 on a side surface of the inner tubular member 31, a tubular hollow fiber membrane bundle 22 consisting of the plurality of porous hollow fiber membranes 3 for gas exchange and wound around an outside surface of an inner tubular member 31, a housing 23 accommodating the tubular hollow fiber membrane bundle 22 together with the inner tubular member 31, partition walls 25 and 26 fixing both end portions of the tubular hollow fiber membrane bundle 22 within the housing in a state where both the ends of the hollow fiber membranes 3 are open, a blood inlet port 28 and blood outlet ports 29a and 29b communicating with a blood chamber 17 formed in the housing 23, and a gas inlet port 24 and a gas outlet port 27 communicating with the inside of the hollow fiber membranes 3.

Figure 4:
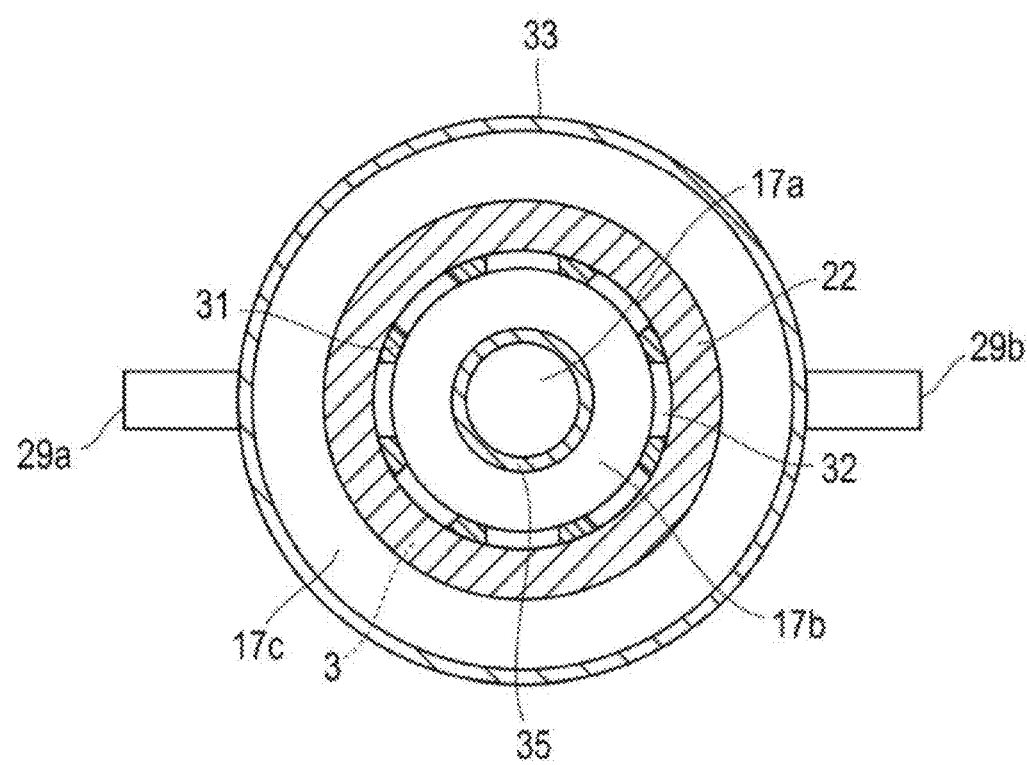
FIG. 4 is a cross-sectional view taken along line IV-IV of FIG. 3.

In the artificial lung 20 of the present embodiment, as shown in FIG. 3 and FIG. 4, the housing 23 has an outer tubular member 33 accommodating the inner tubular member 31, the tubular hollow fiber membrane bundle 22 is accommodated between the inner tubular member 31 and the outer tubular member 33. In accordance with an exemplary embodiment, the housing 23 has one of the blood inlet port or the blood outlet port communicating with the inside of the inner tubular member, and the other one of the blood inlet port or the blood outlet port communicating with the inside of the outer tubular member.

In the artificial lung 20 of the present embodiment, the housing 23 has an inner tubular body 35 that is accommodated in the outer tubular member 33 and the inner tubular member 31, and in which a distal end of the inner tubular body 35 is open in the inner tubular member 31. The blood inlet port 28 is formed on one end (lower end) of the inner tubular body 35, and the two blood outlet ports 29a and 29b extending outwards are formed on a side surface of the outer tubular member 33. There may be one or a plurality of the blood outlet ports.

The tubular hollow fiber membrane bundle 22 is wound around the outside surface of the inner tubular member 31. That is, the inner tubular member 31 is a core of the tubular hollow fiber membrane bundle 22. A distal end portion of the inner tubular body 35 accommodated inside the inner tubular member 31 is open in the vicinity of the first partition walls 25. In addition, the blood inlet port 28 is formed on a protruding lower end portion by the inner tubular member 31.

In accordance with an exemplary embodiment, for each of the inner tubular bodies 35, the inner tubular member 31 where the hollow fiber membrane bundle 22 is wound around the outside surface of the inner tubular member 31, and the outer tubular member 33 is arranged almost concentrically. One end (upper end) of the inner tubular member 31 where the hollow fiber membrane bundle 22 is wound around the outside surface of the inner tubular member 31, and one end (upper end) of the outer tubular member 33 maintain the concentric positional relationship between each other by the first partition walls 25, and are in the liquid-tight state where a space formed between the inside of the inner tubular member 31, and the outer tubular member 33 and the outside surfaces of the hollow fiber membrane bundle 22 does not communicate with the outside.

Furthermore, a portion that is in a slightly upper position than the blood inlet port 28 of the inner tubular body 35, the other end (lower end) of the inner tubular member 31 where the hollow fiber membrane bundle 22 is wound around the outside surface of the inner tubular member 31, and the other end (lower end) of the outer tubular member 33 maintain the concentric positional relationship between each other by the second partition walls 26. The above components are in a liquid-tight state where a space formed between the inner tubular body 35 and the inner tubular member 31, and a space formed between the outside surface of the hollow fiber membrane bundle 22 and the outer tubular member 33 do not communicate with the outside. Furthermore, the partition walls 25 and 26 are formed by a potting agent such as polyurethane and silicone rubber.

The artificial lung 20 of the present embodiment includes a blood inlet portion 17a formed by the inside of the inner tubular body 35, a first blood chamber 17b that is a substantially tubular space formed between the inner tubular body 35 and the inner tubular member 31, and a second blood chamber 17c that is a substantially tubular space formed between the hollow fiber membrane bundle 22 and the outer tubular member 33, and thereby the blood chamber 17 is formed.

The blood flowing from the blood inlet port 28 flows into the blood inlet portion 17a, moves up in the inner tubular body 35 (blood inlet portion 17a), flows out from an upper end 35a (opening end) of the inner tubular body 35, flows into the first blood chamber 17b, passes through an opening 32 formed in the inner tubular member 31, comes into contact with the hollow fiber membranes, and after gas exchange, flows into the second blood chamber 17c, and flows out from the blood outlet ports 29a and 29b.

Furthermore, a gas inlet member 41 having the gas inlet port 24 is fixed to one end of the outer tubular member 33, and similarly, a gas outlet member 42 having the gas outlet port 27 is fixed to the other end of the outer tubular member 33. The blood inlet port 28 of the inner tubular body 35 protrudes through the gas outlet member 42.

The outer tubular member 33 is not particularly limited, and a member having a tubular body, a polygonal tube, an elliptical shape in the cross section, and the like can be used. The member can be the tubular body. Furthermore, an inner diameter of the outer tubular member is not particularly limited, and the inner diameter of the outer tubular member can be any diameter suitable for use in an artificial lung. The diameter is preferably, for example, approximately 32 mm to 164 mm. Furthermore, an effective length of the outer tubular member (that is, the portion of the entire length of the outer tubular member that is not buried in the partition walls) is not particularly limited, and the length can be any effective length of the outer tubular member suitable for use in an artificial lung. The effective length of the outer tubular member is preferably, for example, approximately 10 mm to 730 mm.

Furthermore, a shape of the inner tubular member 31 is not particularly limited, and for example, a member having a tubular body, a polygonal tube, an elliptical shape in a cross section, and the like can be used. The shape is can be the tubular body. Furthermore, an outer diameter of the inner tubular member is not particularly limited, and the outer diameter can be any outer diameter of the inner tubular member suitable for use in an artificial lung. The outer diameter is preferably, for example, approximately 20 mm to 100 mm. Furthermore, the effective length of the inner tubular member (that is, the portion of the length of the inner tubular member that is not buried in the partition walls) is not particularly limited, and the length can be any effective length of the inner tubular member suitable for use in an artificial lung. The effective length of the inner tubular member is preferably, for example, approximately 10 mm to 730 mm.

Figure 5:
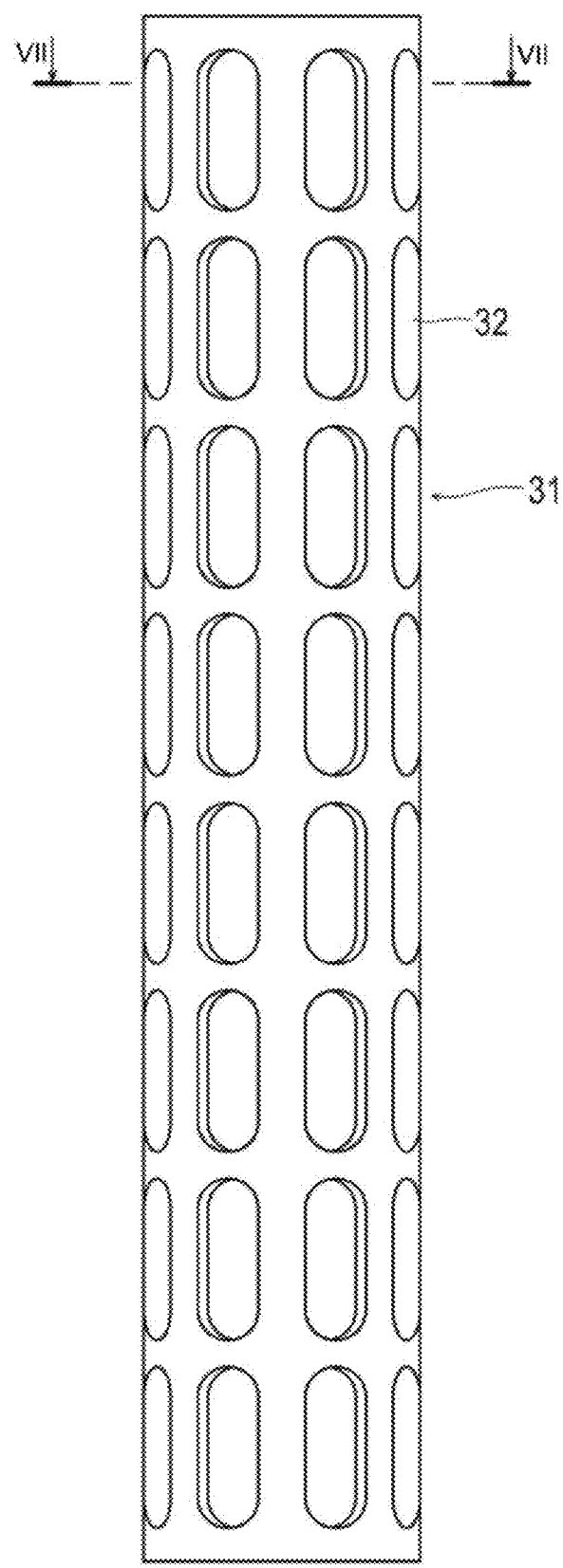
FIG. 5 is a front view showing an example of an inner tubular member used for the hollow fiber membrane artificial lung of an outside blood flow type according to the present disclosure.
Figure 6:
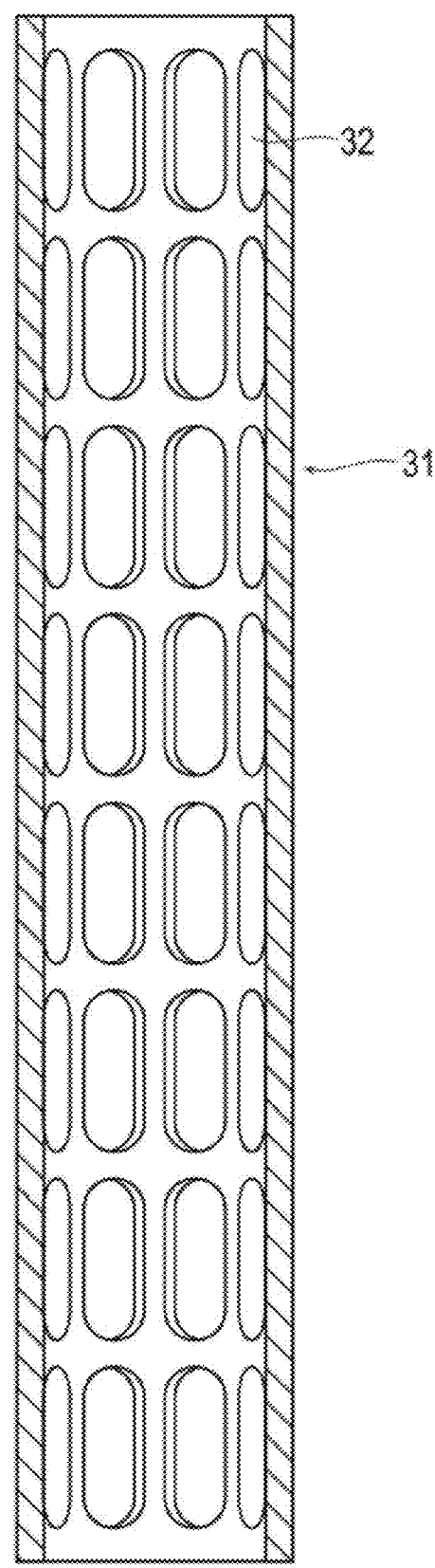
FIG. 6 is a central longitudinal cross-sectional view of the inner tubular member shown in FIG. 5.
Figure 7:
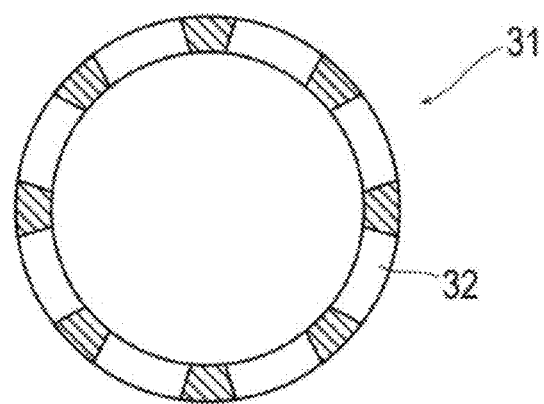
FIG. 7 is a cross-sectional view taken along line VII-VII of FIG. 5.

In accordance with an exemplary embodiment, the inner tubular member 31 includes a large number of the blood circulation openings 32 on the side surface of the inner tubular member 31. For example, regarding a size of the opening 32, it is preferable, for example, that a total area is large as long as the required strength of the tubular member is maintained. As a tubular member satisfying such conditions, for example, a tubular member in which a plurality of sets (8 sets/circumference in the drawing) of a circularly arranged opening in which a plurality (for example, 4 pieces to 24 pieces, and 8 pieces in a longitudinal direction in the drawing) of the openings 32 are provided on an outer peripheral surface of the tubular member at an equal angle and interval, are provided in the axial direction of the tubular member at an equal interval, is favorable as shown in FIG. 5 that is a front view, FIG. 6 that is a central longitudinal cross-sectional view of FIG. 5, and FIG. 7 that is a cross-sectional view taken along line VII-VII of FIG. 5. Furthermore, an opening shape may be a circle, a polygon, an ellipse, and the like, but an oval shape can be preferable as shown in FIG. 5.

In addition, a shape of the inner tubular body 35 is not particularly limited, and for example, a body having a tubular body, a polygonal tube, an elliptical shape in the cross section, and the like can be used. The inner tubular body is preferably, for example, a tubular body. Furthermore, a distance between a distal end opening of the inner tubular body 35 and the first partition walls 25 is not particularly limited, and any distance suitable for use in an artificial lung can be applied. The distance can be, for example, approximately 20 mm to 50 mm. Furthermore, an inner diameter of the inner tubular body 35 is not particularly limited, and the inner diameter can be any inner diameter of the inner tubular body suitable for use in an artificial lung. For example, the inner diameter of the inner tubular body can be approximately 10 mm to 30 mm.

A thickness of the tubular hollow fiber membrane bundle 22 is not particularly limited, and the thickness can be any thickness of the tubular hollow fiber membrane bundle suitable for use in an artificial lung. The thickness of the tubular hollow fiber membrane bundle 22 is preferably, for example, 5 mm to 35 mm, and more preferably, for example, 10 mm to 28 mm. Furthermore, a filling rate of the hollow fiber membranes with respect to the tubular space formed by a space between the outside surface of the tubular hollow fiber membrane bundle 22 and the inside surface is not particularly limited, and the filling rate can be any filling rate suitable for use in an artificial lung. The filling rate can be preferably, for example, 40% to 85%, and more preferably, for example, 45% to 80%. Furthermore, an outer diameter of the hollow fiber membrane bundle 22 can the outer diameter of the hollow fiber membrane bundle suitable for use in an artificial lung. The outer diameter of the hollow fiber membrane bundle can be, for example, 30 mm to 170 mm, and more preferably, for example, 70 mm to 130 mm. As a gas exchange membrane, the membrane described above is used.

In accordance with an exemplary embodiment, the hollow fiber membrane bundle 22 can be formed by winding the hollow fiber membranes around the inner tubular member 31, for example, using the inner tubular member 31 as a core, forming a hollow fiber membrane bobbin, fixing both ends of the formed hollow fiber membrane bobbin by the partition walls, and then cutting both the ends of the hollow fiber membrane bobbin together with the inner tubular member 31 that is a core. The hollow fiber membranes become open on the outside surface of the partition walls by this cutting. A method for forming hollow fiber membranes is not limited to the above method, and any suitable method for forming hollow fiber membranes can be used or appropriately modified.

In accordance with an exemplary embodiment, for example, it is preferable that one or a plurality of the hollow fiber membranes are wound around the inner tubular member 31 substantially in parallel at the same time such that adjacent hollow fiber membranes have a substantially constant interval. Therefore, blood drift can be more effectively suppressed. In addition, a distance between the hollow fiber membrane and an adjacent hollow fiber membrane is not limited to the following, but the distance is preferably, for example, 1/10 to 1/1 of the outer diameter of the hollow fiber membranes. Furthermore, the distance between the hollow fiber membrane and an adjacent hollow fiber membrane is preferably, for example, 30μ to 200 μm.

Furthermore, it is preferable that the hollow fiber membrane bundle 22 is formed by one or a plurality (preferably, for example, 2 membranes to 16 membranes) of the hollow fiber membranes being wound around the inner tubular member 31 at the same time such that all adjacent hollow fiber membranes have a substantially constant interval. For example, the hollow fiber membrane bundle 22 can be formed by the hollow fiber membranes being wound around the inner tubular member 31 according to movement of a rotator for rotating the inner tubular member 31 and a winder for interweaving the hollow fiber membranes under the condition in Expression (1) when winding the hollow fiber membranes around the inner tubular member.

$$\text{Traverse [mm/lot]} \times n \text{ (integer)} = \text{traverse amplitude} \times 2 \pm (\text{outer diameter of fiber} + \text{interval}) \times \text{the number of windings} \qquad \text{Equation (1):}$$

In accordance with an exemplary embodiment, it is possible to further reduce the formation of blood drift by setting the condition as above. The variable n in Expression (1) represents a ratio between the number of rotations of the rotator for winding and the number of reciprocations of the winder at this time, is not particularly limited, but is generally, for example, 1 to 5, and preferably, for example, 2 to 4.

The artificial lung according to another embodiment above is a type in which the blood flows from the inside of the tubular hollow fiber membrane bundle 22, and after passing through the hollow fiber membrane bundle 22, flows to the outside of the hollow fiber membrane bundle 22, and then flows out from the artificial lung 20, but the artificial lung 20 is not limited to the type in which the blood flows from the inside of the tubular hollow fiber membrane bundle 22. For example, the artificial lung 20 may be a type in which the blood flows from the outside of the tubular hollow fiber membrane bundle 22, and after passing through the hollow fiber membrane bundle 22, flows to the inside of the hollow fiber membrane bundle 22, and then flows out from the artificial lung 20.

Furthermore, also in the hollow fiber membrane type artificial lung 20, it is preferable that the antithrombotic high-molecular compound 18 according to the present disclosure coats at least the outer surface 3a' (and optionally, outer surface layer 3a) of the hollow fiber membranes 3 of this hollow fiber membrane type artificial lung 1, as shown in FIG. 2. Herein, the antithrombotic high-molecular compound may exist on an internal layer 3b or an inner surface layer 3c of the hollow fiber membranes 3, but it is preferable that no substantial polymer exists on the internal layer 3b or the inner surface layer 3c of the hollow fiber membrane. Furthermore, the hollow fiber membranes 3 include, in the center, a passage (lumen) 3d forming the gas chamber. In addition, the hollow fiber membranes 3 include an opening portion 3e through which the outer surface 3a' of the opening portion 3e and the inner surface 3c' communicate. The dimensions of the hollow fiber membranes (inner diameter, outer diameter, wall thickness, porosity, pore diameter of pores, and the like) is not particularly limited, but the same aspect as described in FIG. 1 above can be adopted.

In the artificial lung 20 according to the present embodiment, the hollow fiber membranes 3 have a bobbin shape in which membranes are in contact with each other and overlapped many times. In the present embodiment, a coat (coating) by the antithrombotic high-molecular compound is selectively formed on the outer surface 3a' of the hollow fiber membrane uniformly. By adopting such a configuration, the leakage of blood (for example, blood plasma components) to the inner surface layer 3c of the hollow fiber membranes can be suppressed or prevented. That is, the leakage of blood (for example, blood plasma components) can be effectively suppressed or prevented by the antithrombotic high-molecular compound selectively coating the outer surface 3a' (furthermore, outer surface layer 3a) of the hollow fiber membranes 3, which is the blood contact portion. For example, in a case where no substantial antithrombotic high-molecular compound according to one aspect of the present disclosure exists on the internal layer 3b and the inner surface layer 3c of the hollow fiber membranes 3, the hydrophobic state of the material is maintained on the internal layer 3b and the inner surface layer 3c of the hollow fiber membranes, and therefore a large amount of blood (for example, blood plasma components) leakage can be further effectively suppressed or prevented. In the present embodiment, the blood flow path is complicated and has many narrow portions, which is excellent for the gas exchange capacity, but the adhesion, attachment, and activation of the platelets deteriorate in some cases compared to the artificial lung of an outside blood flow type which is not a bobbin type. However, as described above, since the coat by the antithrombotic high-molecular compound is uniform, the adhesion and attachment, and activation of the platelets in the blood contact portion of the hollow fiber membranes occur less. Furthermore, separation of the coating from the hollow fiber membranes (for example, a portion where coating is uneven) can be suppressed or prevented.

In addition, the coat of the antithrombotic high-molecular compound is formed on the outer surface of the hollow fiber membranes of the artificial lung. The coating may be formed on another constituent member (for example, on the entire blood contact portion) in addition to the outer surface. The adhesion, attachment, and activation of the platelets can be further effectively suppressed or prevented in the entire blood contact portion of the artificial lung. In addition, since a contact angle of the blood contact surface decreases, this can facilitate a priming operation. In an exemplary embodiment, the coat of the antithrombotic high-molecular compound is preferably formed on the other constituent member in contact with the blood. For example, the antithrombotic high-molecular compound does not coat a portion other than the blood contact portion of the hollow fiber membranes, or another portion of the hollow fiber membranes (for example, a portion buried in the partition walls, and contact portions of hollow fibers). Such a portion is not in contact with the blood, and therefore the antithrombotic high-molecular compound not being coated thereon does not cause a particular problem.

EXAMPLES

The effects of the present disclosure will be explained using the following examples and comparative examples. But the technical scope of the present disclosure is not only limited to the following examples. In the following examples, the operation was carried out at room temperature (25° C.) unless otherwise specified. In addition, unless otherwise specified, "%" and "part" mean "% by mass" and "parts by mass," respectively.

Synthesis of Antithrombotic High-Molecular Compound

Production Example 1: Synthesis of PMEA with Weight-Average Molecular Weight of 420,000

80 g (0.61 mol) of 2-methoxyethyl acrylate (MEA) was dissolved in 115 g of methanol and put in a 4-neck flask, $N_2$ bubbling was carried out at 50° C. for 1 hour, and thereby a monomer solution was prepared. Additionally, 0.08 g of 2,2'-azobis(4-methoxy-2,4-dimethylvaleronitrile) (V-70, manufactured by Wako Pure Chemical Industries, Ltd.) was dissolved in 5 g of methanol, and a polymerization initiator solution was prepared. Next, this polymerization initiator solution was added to the monomer solution, and the polymerization reaction was carried out at 50° C. for 5 hours. After polymerization for a predetermined time, the polymerization solution was added dropwise to ethanol, and the precipitated polymer (PMEA) was recovered. A weight-average molecular weight of the recovered polymer was measured and was 420,000.

Preparation of Coating Solution

Example 1-1: Coating Solution with PMEA Concentration of 0.1% by Mass 0.4 g of PMEA (a weight-average molecular weight=420,000) synthesized in Production Example 1 was dissolved in 20 g of methanol. 370 g of distilled water was added to a separate vessel, and while stirring with a stirrer, the methanol solution of PMEA was added to the separate vessel with the distilled water at an addition rate of 20 g/min. Thereafter, the mixture was stirred at 25° C. for 10 minutes, and thereby a cloudy coating solution (1) was obtained. The coating solution (1) was a colloidal solution in which a colloid of PMEA was dispersed.

Example 1-2: Coating Solution with PMEA Concentration of 0.3% by Mass

A coating solution (2) was obtained in the same manner as in Example 1-1 except that an amount of PMEA used in Example 1-1 was changed to 1.2 g. The coating solution (2) was a colloidal solution in which a colloid of PMEA was dispersed.

Production of Artificial Lung

Example 2-1

A hollow fiber membrane artificial lung of outside blood flow type (a), in which a membrane area (an area of an outer surface of a hollow fiber membrane) is 0.5 m² and to which porous hollow fiber membranes for gas exchange made of porous polypropylene are wound, was produced, the hollow fiber membrane having an inner diameter of 195 μm, an outer diameter of 295 μm, a wall thickness of 50 μm, porosity of about 35% by volume, a pore diameter of an outer surface (that is, an average diameter of an opening portion) of 80 nm.

In a state where a blood flow path of the artificial lung (a) was filled with the coating solution (1) prepared in Example 1-1, carbon dioxide gas was circulated at a flow rate of 2 L/min for 2 minutes to a gas circulating side (an inner surface side). Thereafter, the coating solution was removed, air of a flow volume of 80 L was allowed to flow to dry the hollow fiber membranes. Thereby, a hollow fiber membrane artificial lung (1) of an outside blood flow type which has hollow fiber membranes (hereinafter, will be simply referred to as the "artificial lung (1)") in which a coating is formed on the outer surface of the hollow fiber membranes was produced.

Example 2-2

A hollow fiber membrane artificial lung of outside blood flow type (2) was produced in the same manner as in Example 2-1 except that a flow time of carbon dioxide gas was changed to 10 minutes in Example 2-1. The hollow fiber membrane artificial lung of outside blood flow type (2) obtained as described above (hereinafter, will be simply referred to as the "artificial lung (2)") was produced.

Example 2-3

A hollow fiber membrane artificial lung of outside blood flow type (3) was produced in the same manner as in Example 2-1 except that a flow time of carbon dioxide gas was changed to 60 minutes in Example 2-1. The hollow fiber membrane artificial lung of outside blood flow type (3) obtained as described above (hereinafter, will be simply referred to as the "artificial lung (3)") was produced.

Comparative Example 2-1

A hollow fiber membrane artificial lung of outside blood flow type (4) was produced in the same manner as in Example 1-1 except that a state where the blood flow path of the artificial lung (a) was filled with the coating solution (1) prepared in Example 2-1, was left to stand for 2 minutes without circulating carbon dioxide gas from a gas circulating side (an inner surface side). The hollow fiber membrane artificial lung of outside blood flow type (4) obtained as described above (hereinafter, will be simply referred to as the "artificial lung (4)") was produced.

Comparative Example 2-2

A hollow fiber membrane artificial lung of outside blood flow type (5) was produced in the same manner as in Comparative Example 2-1 except that the coating solution (1) used in Comparative Example 2-1 was changed to the coating solution (2). The hollow fiber membrane artificial lung of outside blood flow type (5) obtained as described above (hereinafter, will be simply referred to as the "artificial lung (5)") was produced.

Experiment 1. Quantitative Determination of Coating Amount

For the artificial lungs (1) to (3) of Examples 2-1 to 2-3, and the artificial lungs (4) and (5) of Comparative Examples 2-1 and 2-2, a coating amount of PMEA was measured by the following method.

The artificial lungs (1) to (5) were respectively disassembled to remove membranes of the artificial lungs. Among them, 3 g of the membrane of the artificial lung was filled in a screw-capped glass tube, 25 ml of acetone was added to the screw-capped glass tube with the membrane, stirring was performed for 120 minutes, and PMEA coated onto the respective membranes of the artificial lungs was extracted. The entirety of the acetone extraction liquid was transferred to another screw-capped glass tube. The acetone was evaporated using a heat block. 10 ml of tetrahydrofuran was added to the glass tube into which an evaporation-dried solid substance was inserted to dissolve the evaporation-dried solid substance. A THF solution (a standard solution) containing 1 mg/ml of PMEA was analyzed using GPC, and an area of a peak corresponding to PMEA was calculated. Subsequently, a THF solution (a test solution) of the evaporation-dried solid substance was analyzed using GPC, and an area of a peak corresponding to PMEA was calculated in the same manner. Thereafter, an amount of PMEA in the test solution was calculated using Equation 1, and a coating amount of PMEA per 1 $m^2$ of the membrane of the artificial lung (an area 1 $m^2$ of an outer surface of the hollow fiber membrane) was calculated using Equation 2. The results are shown in Table 1.

$$\text{Amount (mg) of PMEA in test solution} = (\text{peak area of test solution/peak area of standard solution}) \times 10 \quad \text{Equation 1:}$$

$$\text{Amount (mg/}m^2\text{) of PMEA coating in artificial lung membrane} = \text{amount of PMEA in test solution/(weight of artificial lung membrane subjected to extraction} \times \text{membrane area per 1 g of artificial lung membrane} \quad \text{Equation 2:}$$

Based on the results of Table 1 (FIG. 8), it was confirmed that, in the artificial lungs (1) to (3) produced by the method according to the present disclosure, a coating amount of PMEA was dramatically increased.

Experiment 2. Test of Antithrombotic Properties

The antithrombotic properties of the artificial lung (1) and the artificial lung (4) obtained in Example 2-1 and Comparative Example 2-1 were evaluated according to the following method.

Each artificial lung was incorporated into the extracorporeal circulation circuit, and filled with 90 ml of fresh porcine blood to which heparin was added, and 110 ml of a saline solution. A concentration of heparin in the circulating blood was 0.5 u/ml. The circulating blood was circulated at room temperature (25° C.) at 500 ml/min. Immediately after the start of the circulation, 0.7 ml of a solution in which protamine sulfate (100 mg/10 mL) was diluted with a saline solution 100-fold was injected into the circulating blood. After 30 minutes, blood from each blood circulation circuit was sampled, the number of platelets was measured, a ratio of the measured number of platelets to the number of platelets before the start of the circulation was calculated, and thereby a maintenance rate of the number of platelets was obtained. As the maintenance rate of the number of platelets in blood becomes high, a degree of the antithrombotic properties becomes high. The results are shown in Table 2 (FIG. 9).

Based on the results in Table 2 (FIG. 9), it can be understood that, in the artificial lung (1) produced by the method according to the present disclosure, the antithrombotic properties are significantly improved by increasing the coating amount of PMEA.

The detailed description above describes to a method for producing an artificial lung and an artificial lung. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for producing an artificial lung including a plurality of porous hollow fiber membranes for gas exchange, the plurality of porous hollow fiber membranes having an outer surface, an inner surface forming a lumen, and an opening portion communicating the outer surface with the inner surface, the method comprising:
   bringing one of the outer surface or the inner surface into contact with a colloidal solution that contains an antithrombotic high-molecular compound; and circulating carbon dioxide gas to a side opposite of the one of the outer surface or the inner surface that is being brought into contact with the colloidal solution containing the antithrombotic high-molecular compound to increase an amount of the antithrombotic high-molecular compound on the one of the outer surface or the inner surface of the plurality of porous hollow fiber membranes.

2. The method for producing an artificial lung according to claim 1, comprising:
circulating 50 mL to 5000 mL of the carbon dioxide gas with respect to 1 g of the colloidal solution.

3. The method for producing an artificial lung according to claim 1, wherein the colloidal solution contains 0.01% by mass or more of the antithrombotic high-molecular compound.

4. The method for producing an artificial lung according to claim 1, comprising:
bringing the outer surface into contact with the colloidal solution containing the antithrombotic high-molecular compound; and
circulating the carbon dioxide gas to a side of the inner surface.

5. The method for producing an artificial lung according to claim 1, wherein the antithrombotic high-molecular compound has a structural unit derived from alkoxyalkyl (meth)acrylate represented by Formula (I):

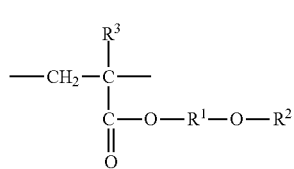

(I)

wherein in Formula (I), $R^3$ represents a hydrogen atom or methyl group, $R^1$ represents an alkylene group having 1 to 4 carbon atoms, and $R^2$ represents an alky group having 1 to 4 carbon atoms.

6. The method for producing an artificial lung according to claim 1, wherein a weight-average molecular weight of the antithrombotic high-molecular compound is between 200,000 and 800,000.

7. The method for producing an artificial lung according to claim 1, wherein the bringing of the outer surface or the inner surface into contact with the colloidal solution that contains an antithrombotic high-molecular compound comprises:
filling or dip coating the outer surface or the inner surface with the colloidal solution that contains the antithrombotic high-molecular compound.

8. The method for producing an artificial lung according to claim 1, comprising:
filling the outer surface or the inner surface with the colloidal solution that contains the antithrombotic high-molecular compound with a filling amount of the colloidal solution of 50 $g/m^2$ to 200 $g/m^2$.

9. The method for producing an artificial lung according to claim 1, further comprising:
circulating an inert gas with the carbon dioxide gas, the inert gas being 0% by volume to 50% by volume.

10. The method for producing an artificial lung according to claim 8, wherein the inert gas is nitrogen.

11. A method for producing an artificial lung including a plurality of porous hollow fiber membranes for gas exchange, the plurality of porous hollow fiber membranes having an outer surface, an inner surface forming a lumen, and an opening portion communicating the outer surface with the inner surface, the method comprising:
bringing the outer surface of the plurality of porous hollow fiber membranes into contact with a colloidal solution that contains an antithrombotic high-molecular compound; and
circulating carbon dioxide gas to the inner surface of the plurality of porous hollow fiber membranes to increase an amount of the antithrombotic high-molecular compound on the outer surface of plurality of porous hollow fiber membranes.

12. The method for producing an artificial lung according to claim 11, wherein the colloidal solution contains 0.01% by mass or more of the antithrombotic high-molecular compound, the method further comprising:
circulating 50 mL to 5000 mL of the carbon dioxide gas with respect to 1 g of the colloidal solution.

13. The method for producing an artificial lung according to claim 11, wherein the antithrombotic high-molecular compound has a structural unit derived from alkoxyalkyl (meth)acrylate represented by Formula (I):

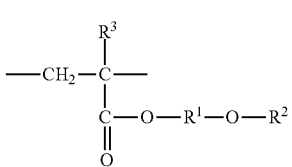

(I)

wherein in Formula (I), $R^3$ represents a hydrogen atom or methyl group, $R^1$ represents an alkylene group having 1 to 4 carbon atoms, and $R^2$ represents an alky group having 1 to 4 carbon atoms; and
wherein a weight-average molecular weight of the antithrombotic high-molecular compound is between 200,000 and 800,000.

14. The method for producing an artificial lung according to claim 11, further comprising:
circulating an inert gas with the carbon dioxide gas, the inert gas being 0% by volume to 50% by volume, and wherein the inert gas is nitrogen.

15. The method according to claim 1, wherein the amount of the antithrombotic high-molecular compound on the one of the outer surface or the inner surface that contains the antithrombotic high-molecular compound is 10 $mg/m^2$ or more.

16. The method according to claim 11, wherein the amount of the antithrombotic high-molecular compound on the outer surface of the plurality of porous hollow fiber membranes is 10 $mg/m^2$ or more.

* * * * *